(12) United States Patent
Kuo et al.

(10) Patent No.: US 11,090,395 B2
(45) Date of Patent: Aug. 17, 2021

(54) COMPOSITION FOR CROSS TALK BETWEEN ESTROGEN RECEPTORS AND CANNABINOID RECEPTORS

(71) Applicant: SeeCure Taiwan Co., Ltd., Kaohsiung (TW)

(72) Inventors: Tsung-Tien Kuo, Kaohsiung (TW); David J. Yang, Sugar Land, TX (US); Wei-Chung Chang, Kaohsiung (TW); Min-Ching Chung, Kaohsiung (TW); Chi-Shiang Ke, Kaohsiung (TW)

(73) Assignee: SeeCure Taiwan Co., Ltd., Kaohsiung (TW)

( * ) Notice: Subject to any disclaimer, the term of this patent is extended or adjusted under 35 U.S.C. 154(b) by 126 days.

(21) Appl. No.: 16/131,045

(22) Filed: Sep. 14, 2018

(65) Prior Publication Data
US 2020/0085978 A1    Mar. 19, 2020

(51) Int. Cl.
A61K 51/04    (2006.01)

(52) U.S. Cl.
CPC ...... A61K 51/0497 (2013.01); A61K 51/0455 (2013.01); A61K 51/0482 (2013.01); A61K 51/0493 (2013.01); A61K 2121/00 (2013.01)

(58) Field of Classification Search
CPC ............ A61K 51/0497; A61K 51/0482; A61K 51/0493; A61K 2121/00; A61P 35/00
See application file for complete search history.

(56) References Cited

U.S. PATENT DOCUMENTS

| 4,952,569 | A | * | 8/1990 | Simons | C07J 17/00 435/7.93 |
| 5,192,525 | A | | 3/1993 | Yang et al. | |
| 5,219,548 | A | | 6/1993 | Yang et al. | |
| 5,238,714 | A | | 8/1993 | Wallace et al. | |
| 6,096,874 | A | * | 8/2000 | Wallace | C07B 59/001 534/10 |
| 8,758,723 | B2 | * | 6/2014 | Yang | A61K 51/0491 424/1.49 |

FOREIGN PATENT DOCUMENTS

| WO | WO 88/08422 | * 11/1988 | ........... C07D 257/02 |
| WO | 2007120153 | 10/2007 | |
| WO | 2008130439 | 10/2008 | |

OTHER PUBLICATIONS

Banerjee et al., Bioorg. Med. Chem., 2005, 13, 2005, p. 4315-4322. (Year: 2005).*
Hunter et al., Bioconjugate Chem., 2000, 11, p. 175-181. (Year: 2000).*
Yasuda et al., CurrentTopics in Steroid Research, 2010, 7, 11-17 (abstract). (Year: 2010).*
Ogura et al. (Biochemical Pharmacology, 2006, 71, p. 1358-1369). (Year: 2006).*
Gums (Stroke, 2004, p. 590-595). (Year: 2004).*
Yasuda et al., Current Topics in Steroid Research, 2010, 7, p. 11-17. (Year: 2010).*
Anelli et al., J. Med. Chem., 2004, 47, p. 3629-3641. (Year: 2004).*
Barge et al., Org. Biomol. Chem., 2009, 7, p. 3810-3816 (Year: 2009).*
Dobovišek L, et al., "Overlapping molecular pathways between cannabinoid receptors type 1 and 2 and estrogens/androgens on the periphery and their involvement in the pathogenesis of common diseases," Int J Mol Med., Oct. 2016, pp. 1642-1651.
Elbaz M, et al., "Novel role of cannabinoid receptor 2 in inhibiting EGF/EGFR and IGF-I/IGF-IR pathways in breast cancer," Oncotarget, vol. 8, May 2017, pp. 29668-29678.
Ford BM, et al., "Tamoxifen Isomers and Metabolites Exhibit Distinct Affinity and Activity at Cannabinoid Receptors: Potential Scaffold for Drug Development," PLoS ONE, vol. 68, Dec. 2016, pp. 1-23.
Franks LN, et al., "Selective Estrogen Receptor Modulators: Cannabinoid Receptor Inverse Agonists with Differential CB1 and CB2 Selectivity," Front Pharmacol., vol. 7, Dec. 2016, pp. 1-16.
Hayashi SI, et al., "The expression and function of estrogen receptor alpha and beta in human breast cancer and its clinical application," Endocr Relat Cancer., Jun. 2003, pp. 193-202.
Prather PL, et al., "CB1 and CB2 receptors are novel molecular targets for Tamoxifen and 4OH-Tamoxifen.," Biochem Biophys Res Commun., vol. 441, Oct. 2013, pp. 339-343.
Speirs V, et al., "Oestrogen receptor beta: what it means for patients with breast cancer," Lancet Oncol., vol. 5, Mar. 2004, pp. 174-181.
Takeda S, et al., "Δ9-Tetrahydrocannabinol Disrupts Estrogen-Signaling through Up-Regulation of Estrogen Receptor β(ERβ)," Chem Res Toxicol., May 2013, pp. 1073-1079.
Greg T. Hermanson, "The Reactions of Bioconjugation—Epoxides and Oxiranes." Bioconjugate Techniques—3rd Edition, Academic Press, Sep. 17, 2013, pp. 236.
"Search Report of Europe Counterpart Application," dated Dec. 4, 2019, p. 1-p. 11.

* cited by examiner

Primary Examiner — Michael G. Hartley
Assistant Examiner — Leah H Schlientz
(74) Attorney, Agent, or Firm — JCIPRNET

(57) ABSTRACT

A composition for cross talk between estrogen receptors and cannabinoid receptors including a chelator and a receptor ligand is provided. A method of synthesizing the composition is also provided, and the composition may be further prepared in pharmaceutical formulations or kits for therapy or molecular imaging.

8 Claims, 30 Drawing Sheets

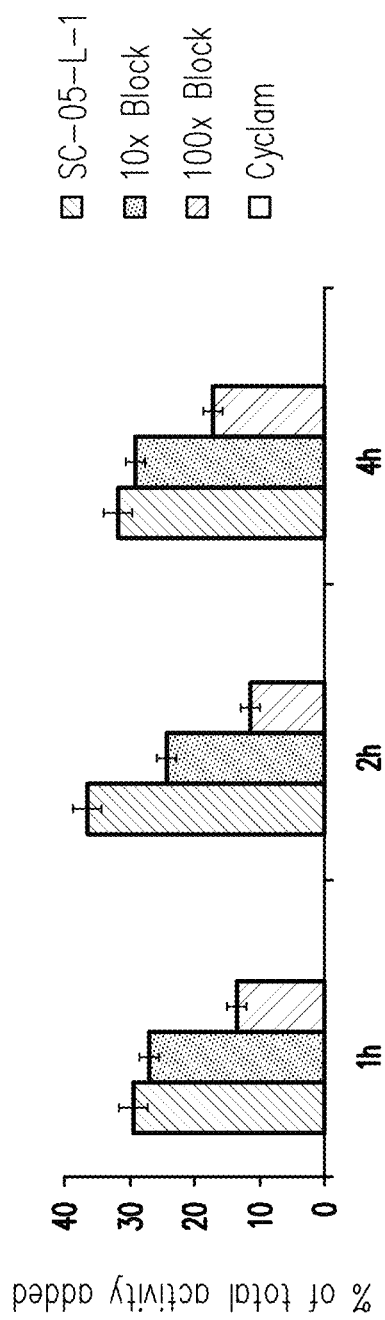
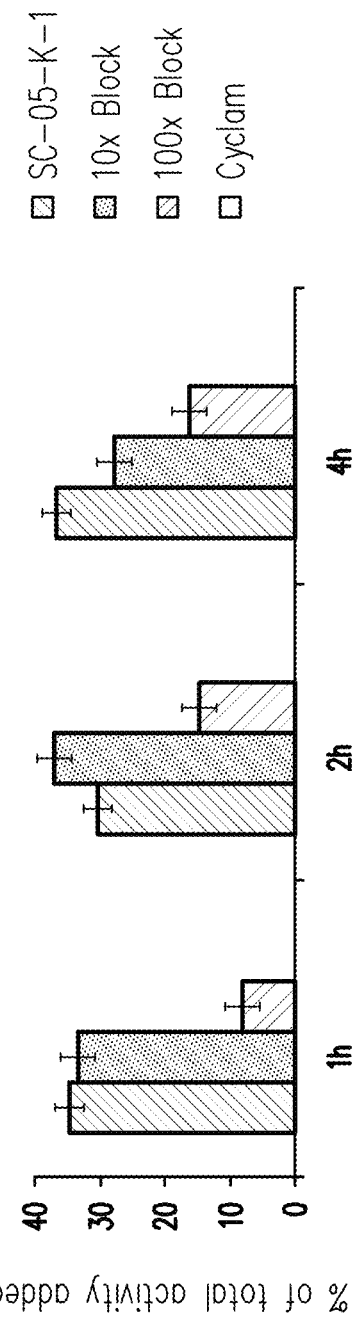
FIG. 3A
FIG. 3B

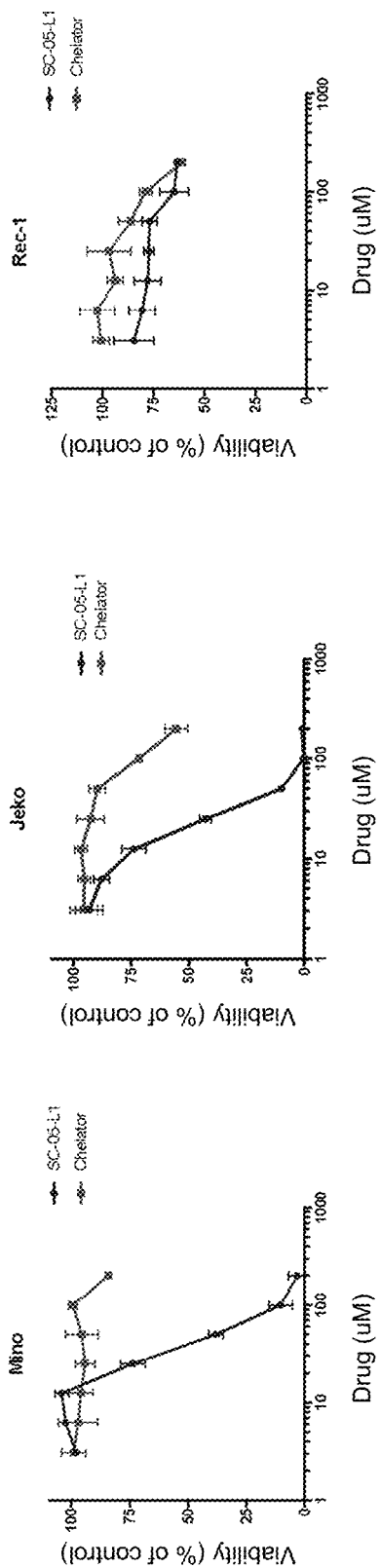
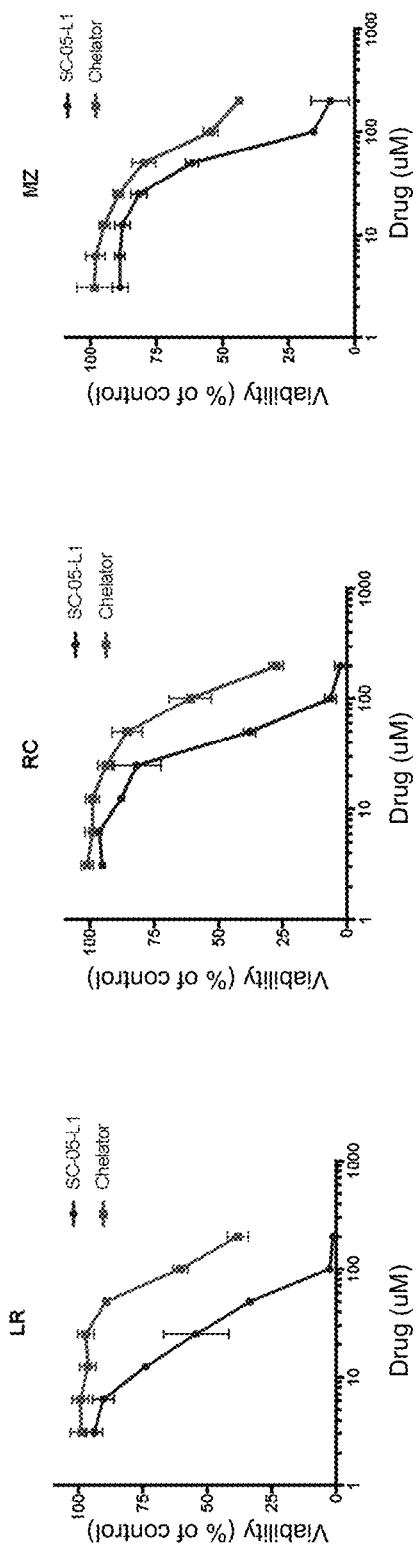
FIG. 7A
FIG. 7B

COMPOSITION FOR CROSS TALK BETWEEN ESTROGEN RECEPTORS AND CANNABINOID RECEPTORS

BACKGROUND

Technical Field

The present invention generally relates to a composition, in particular, to a composition for cross talk between estrogen receptors and cannabinoid receptors, a method of synthesizing the same, a kit, and an imaging method and a treatment method using the same.

Description of Related Art

Currently assessment of disease status relies on computed tomography (CT), magnetic resonance imaging (MRI), x-ray or ultrasound. These modalities provide morphological (size, shape) and anatomical information. In addition to these imaging modalities, the treatment endpoints rely almost exclusively on the analysis of biopsies by molecular and histopathological methods which provide a microscopic picture of the general heterogeneous process. However, these prognostic tools do not provide cellular target information, thus, assessment of the effectiveness of therapy is not at optimal.

The development of radiolabeled biochemical compounds to understand molecular pathways has expanded the use of nuclear molecular imaging studies in drug development. Positron emission tomography (PET) and single photon emission computed tomography (SPECT) use radiopharmaceuticals to image, map, and measure target site activities (e.g. angiogenesis, metabolism, hypoxia, apoptosis and proliferation). PET and SPECT agents are also known as micro-dosing agents because there are no detectable pharmacologic effects. [$^{18}$F]Fluorodeoxyglucose (FDG), a gold standard for PET, is complementary to the CT and MRI and allows detection of unsuspected distant metastases. Though PET FDG was concordant with the findings of CT and MRI in diagnosing various tumors, FDG also has a drawback. For instance, a significant amount (>95%) of FDG was concentrated in mitochondria fraction and this resulted in an apparent false-positive lesion between inflammation/infection and tumor recurrence. In addition, FDG could not provide accurate information on the prediction of therapeutic response. Thus, it is amenable to develop a radiopharmaceutical beyond FDG that can provide therapeutic indications.

SUMMARY

Accordingly, the present invention provides a composition for cross talk between estrogen receptors (ERs) and cannabinoid receptors (CBRs) and a novel method of synthesizing the same. The composition may be further prepared in pharmaceutical formulations or kits for therapy or molecular imaging.

The invention provides a composition for cross talk between estrogen receptors and cannabinoid receptors including a chelator and a receptor ligand.

In an embodiment of the invention, the chelator is a nitrogen containing tetraazacyclic ring.

In an embodiment of the invention, the nitrogen containing tetraazacyclic ring is a cyclam, a cyclen, a cyclam-carboxylic acid, or a cyclen-carboxylic acid.

In an embodiment of the invention, the receptor ligand is an estrogen ligand or an anti-estrogen ligand.

In an embodiment of the invention, the estrogen ligand includes estradiol, estrone, estiol, and clomiphene.

In an embodiment of the invention, the anti-estrogen ligand includes non-steroidal tamoxifen, torimiphene, raloxifen, and aminoglutethimide.

In an embodiment of the invention, the receptor ligand has a spacer hydroxy group.

In an embodiment of the invention, the composition further includes a metal ion.

In an embodiment of the invention, the metal ion is a radionuclide, a non-radioactive metal, or a combination thereof.

In an embodiment of the invention, the radionuclide is $^{99m}$Tc, $^{67,68}$Ga, $^{60,61,62,64,67}$Cu, $^{111}$In, $^{166}$Ho, $^{186,188}$Re, $^{90}$Y, $^{177}$Lu, $^{223}$Ra, $^{225}$Ac, and $^{89}$Zr, $^{117m}$Sn, $^{153}$Sm, $^{89}$Sr, $^{59}$Fe, $^{212}$Bi, $^{211}$At, $^{45}$Ti, or a combination thereof.

In an embodiment of the invention, the non-radioactive metal is a technetium ion (Tc), a stannous ion (Sn), a copper ion (Cu), an indium ion (In), a thallium ion (Tl), a gallium ion (Ga), an arsenic ion (As), a rhenium ion (Re), a holmium ion (Ho), a yttrium ion (Y), a samarium ion (Sm), a selenium ion (Se), a strontium ion (Sr), a gadolinium ion (Gd), a bismuth ion (Bi), an iron ion (Fe), a manganese ion (Mn), a lutecium ion (Lu), a cobalt ion (Co), a platinum ion (Pt), a calcium ion (Ca), a rhodium ion (Rh), an europium ion (Eu), and a terbium ion (Tb), or a combination thereof.

In an embodiment of the invention, the composition is a $^{99m}$Tc-cyclam-tamoxifen analogue or a $^{99m}$Tc-cyclen-tamoxifen analogue.

The invention also provides a kit including the composition described above.

The invention further provides a method of synthesizing the composition described above.

In an embodiment of the invention, the receptor ligand is conjugated to a tetracyclic ring with an epoxide.

In an embodiment of the invention, the epoxide is attached to an aliphatic chain of the receptor ligand.

The invention further provides an imaging method for cancer, rheumatoid arthritis, osteoporosis, atherosclerosis, or endometrial tissue including administration of the composition described above.

In an embodiment of the invention, an image is a gamma image, a PET image, a PET/CT image, a SPECT image, a SPECT/CT image, a PET/MRI image, a SPECT/MRI image, or a hybrid image.

In an embodiment of the invention, an imaging dose is defined as a kit.

The invention further provides a treatment method for cancer, rheumatoid arthritis, osteoporosis, atherosclerosis, or endometrial tissue including administration of the composition described above.

Based on the above, the present invention provides the composition for cross talk between the estrogen receptors and the cannabinoid receptors. The hydroxy group is incorporated in the finished product. In the composition of the present invention, the protected chelator is used as to react the expoxylated receptor ligand to form the chelator-receptor ligand conjugate. The technology platform may exploit conjugating antagonists and agonists and seeing their effects in various forms of diseases. Also, the composition may be further prepared in pharmaceutical formulations and kits using chemical procedures known to skilled artisans. In addition, the method of synthesizing the composition is also provided, and the synthesis method may obviate the need of adding protecting groups to the receptor ligand and increase process efficiency and purify of the final product. Besides, the composition of the present invention may be used for imaging or treating estrogen receptors and cannabinoid receptors associated diseases.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

FIG. 3A and FIG. 3B show the MCF-7 cell uptake and blocking studies of Composition $^{99m}$Tc-SC-05-K-1 and Composition $^{99m}$Tc-SC-05-L-1 synthesized in Example 2 and Example 4 of the invention.

FIG. 7A and FIG. 7B show the in vitro anti-cancer studies of Composition SC-05-L-1 synthesized in Example 3 of the invention.

DESCRIPTION OF THE EMBODIMENTS

Figure 1A:
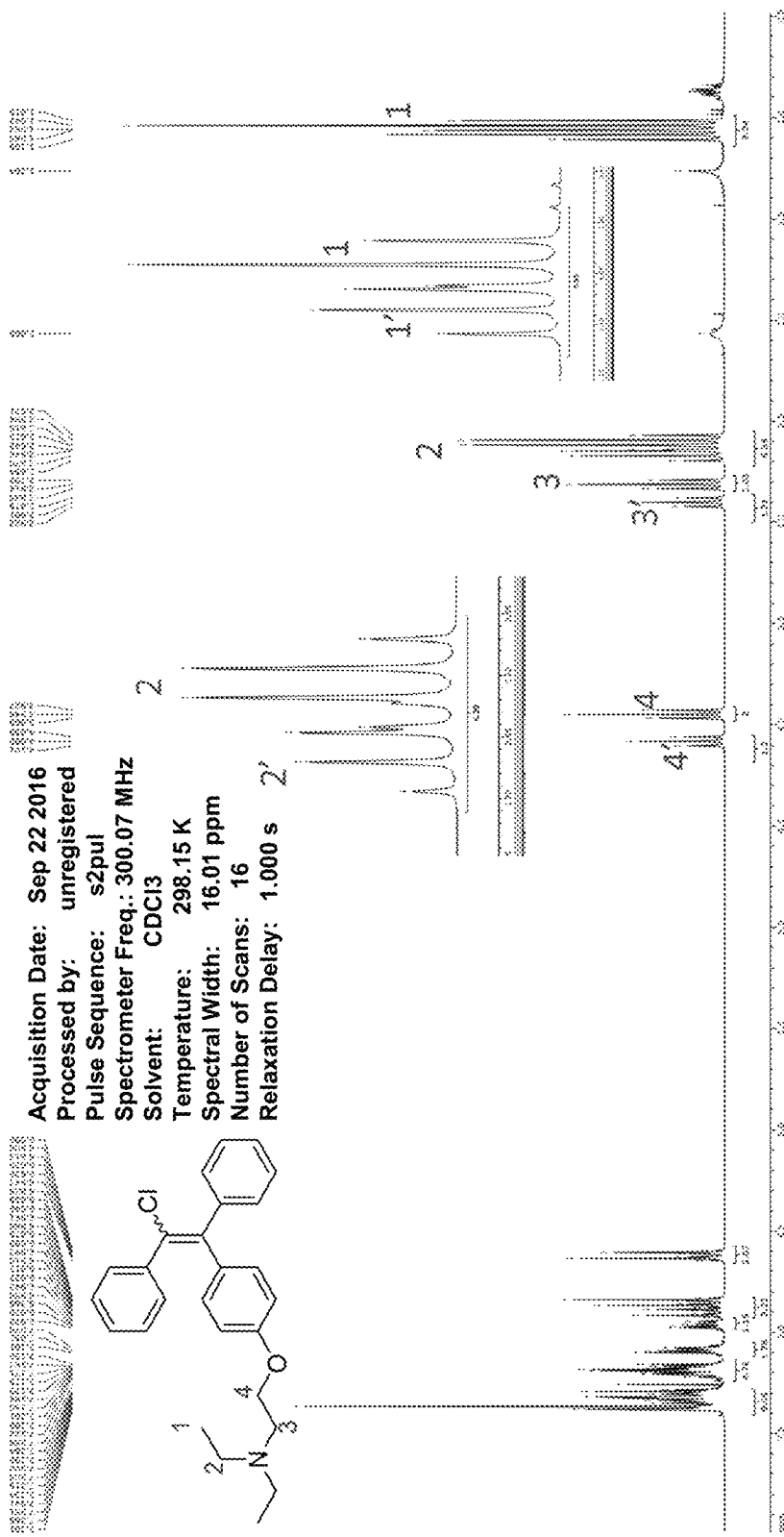
FIG. 1A shows the $^1$H-NMR spectrum of Compound 1 synthesized in Example 1 of the invention.

Reference will now be made in detail to the present preferred embodiments of the invention, examples of which are illustrated in the accompanying drawings. Wherever possible, the same reference numbers are used in the drawings and the description to refer to the same or like parts.

Assessment of estrogen receptor-positive (ER+) pathway activated systems is the basis of hormone-dependent disease management. ER+ patients respond better to endocrine therapy and survived twice as long as negative ER patients. However, tumor resistance to antiestrogens is un-predictable. The drug resistance may be due to its poor or slow uptake by the tumor. A selective estrogen receptor modulator (SERM) could produce cross talk between ERs and cannabinoid receptors (CBR) pathway systems. Identify whether the SERM-based drug uses CBR as an active transport strategy could enhance drug to ER binding pocket and may overcome drug resistance. Accordingly, the present invention provides a composition for cross talk between the estrogen receptors and the cannabinoid receptors including a chelator and a receptor ligand.

In some embodiments, the chelator may be a nitrogen containing tetraazacyclic ring, for example. Specifically, the nitrogen containing tetraazacyclic ring may be a cyclam, a cyclen, a cyclam-carboxylic acid, or a cyclen-carboxylic acid, for example, but the invention is not limited thereto.

In some embodiments, the receptor ligand may be an estrogen ligand or an anti-estrogen ligand, for example. In some embodiments, the estrogen ligand may include estradiol, estrone, estiol, and clomiphene, for example. In some other embodiments, the anti-estrogen ligand may include, non-steroidal tamoxifen, torimiphene, raloxifen, and aminoglutethimide, for example. However, the invention is not limited thereto. In some embodiments, the receptor ligand has a spacer hydroxy group which will be described in detail below.

In some embodiments, the composition further includes a metal ion. Specifically, the metal ion may be a radionuclide, a non-radioactive metal, or a combination thereof, for example. In some embodiments, the radionuclide may be $^{99m}$Tc, $^{67,68}$Ga, $^{60,61,62,64,67}$Cu, $^{111}$In, $^{166}$Ho, $^{186,188}$Re, $^{90}$Y, $^{177}$Lu, $^{223}$Ra, $^{225}$Ac, and $^{89}$Zr, $^{117m}$Sn, $^{153}$Sm, $^{89}$Sr, $^{59}$Fe, $^{212}$Bi, $^{211}$At, $^{45}$Ti, or a combination thereof, for example. In some other embodiments, the non-radioactive metal may be a technetium ion (Tc), a stannous ion (Sn), a copper ion (Cu), an indium ion (In), a thallium ion (Tl), a gallium ion (Ga), an arsenic ion (As), a rhenium ion (Re), a holmium ion (Ho), a yttrium ion (Y), a samarium ion (Sm), a selenium ion (Se), a strontium ion (Sr), a gadolinium ion (Gd), a bismuth ion (Bi), an iron ion (Fe), a manganese ion (Mn), a lutecium ion (Lu), a cobalt ion (Co), a platinum ion (Pt), a calcium ion (Ca), a rhodium ion (Rh), an europium ion (Eu), and a terbium ion (Tb), or a combination thereof, for example. However, the invention is not limited thereto. In one specific embodiment of the invention, the composition may be a $^{99m}$Tc-cyclam-tamoxifen analogue. In another specific embodiment of the invention, the composition may be a $^{99m}$Tc-cyclen-tamoxifen analogue.

It should be mentioned that the composition of the present invention may be used to identify the ER+ pathways through cell surface CBRs. Radiolabeled ER+ ligand is not only able to quantify ER+ tissue uptake to stage and re-stage of the cancer, but also able to select the patients for optimal response to therapy as well as to discontinue the treatment when resistance occurs. In other words, due to the structure of the composition, the composition may enhance drug to ER binding pocket by an active transport strategy, thereby overcoming the drug resistance.

The present invention further provides a method of synthesizing the composition. The steps of the synthesis method are described in detail below, but the invention is not limited thereto.

In some embodiments, the receptor ligand is conjugated to a tetracyclic ring with an epoxide first, for example. In other words, the epoxide is attached to an aliphatic chain of the receptor ligand. In some embodiments, the receptor ligand may be an estrogen agonist, an estrogen antagonist, or an aromatase inhibitor including non-steroidal derivatives of clomiphene, tamoxifen, raloxifene, torimiphene and aminoglutethimide, for example. In one specific embodiment of the invention, the anti-estrogen is tamoxifen, but the invention is not limited thereto. Specifically, a chlorinated epoxide (spacer) is reacted with aliphatic hydroxylated tamoxifen in an organic solvent, thereby producing the epoxide-tamoxifen. In this case, the receptor ligand is tamoxifen, a selective estrogen receptor modulator (SERM), could produce crosstalk between estrogen receptors and cannabinoid receptors pathway systems, but the invention is not limited thereto. Then, the epoxide-tamoxifen is reacted with a protected tetraazacyclic chelator including coupling agents. Thus, a hydroxy group is positioned at the chelator-tamoxifen conjugate in the finished product. In some embodiments, the tetraazacyclic chelators may be a cyclam or a cyclen, for example. However, the invention is not limited thereto. It should be noted that the hydroxyl group is located at the aliphatic chain of the receptor ligands. To be clearly understood, Scheme 1 shows a schematic diagram illustrating the receptor ligand (R) conjugated to the cyclam or the cyclen as shown below:

Scheme 1: The receptor ligand (R) is conjugated to the cyclam or the cyclen

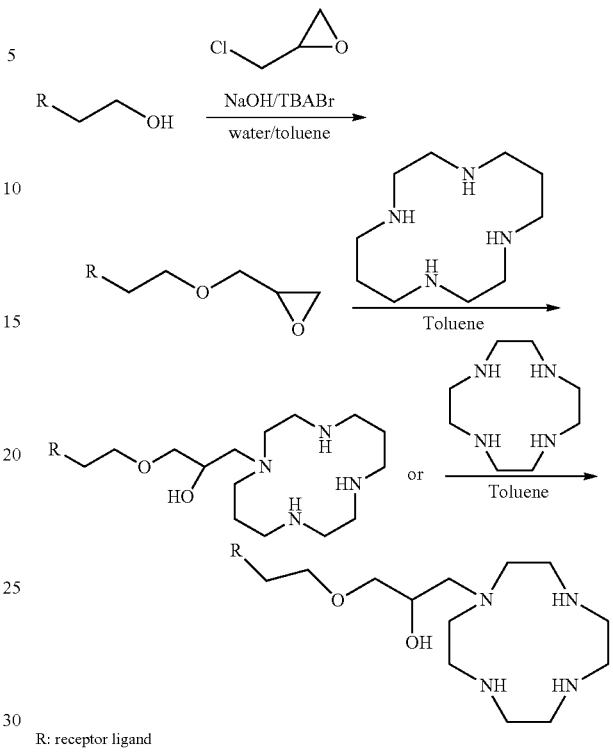

R: receptor ligand

In some embodiments, a method of admixing may be carried out in an organic solvent, such as dimethylformamide, dimethylsulfoxide, dioxane, methanol, ethanol, hexane, methylene chloride, acetonitrile, tetrahydrofuran, or a mixture thereof. In other embodiments, the method of admixing may be carried out in an aqueous solvent. In some embodiments, one, two, or three of the nitrogen groups of the chelator may be protected, for example, by a tert-butyl or benzyl group, or unprotected.

In some embodiments, the method of the present invention may further include at least one purification step. Any compound of the present invention may be purified via any method known to those of skill in the art. Persons of skill in the art are familiar with such methods, and when those methods may be employed. For example, in a multi-step synthesis that is aimed at arriving at a particular compound, a purification step may be performed after every synthetic step, after every few steps, at various points during the synthesis, and/or at the very end of the synthesis. In some embodiments, one or more purification steps includes technique selected from the group consisting of silica gel column chromatography, HPLC (high-performance liquid chromatography) and LC (liquid chromatography). In certain embodiments, purification methods specifically exclude size exclusion chromatography and/or dialysis. It should be noted that the method of synthesizing the composition in organic solvents and the use of protecting groups, typically offer improvements in the purification of compounds. The installation of protecting groups permits various functional groups of intermediates during the synthesis to be protected, and facilitates the purification of those intermediates. Various means of purification using organic solvents allow for separation and isolation of desired compounds, such as imaging agents, with very little impurities. Thus, it is amenable to develop organic synthetic techniques to allow for site-specific conjugates of higher purities to be obtained in a more efficient way.

In one specific embodiment of the invention, the hydroxylated tamoxifen is conjugated to the cyclam and the cyclen at one nitrogen group using the synthetic route as shown in Scheme 2 and Scheme 3 below. In this case, a hydroxy group is incorporated in the finished product. The protected chelator is used as to react an epoxylated tamoxifen to form a chelator-tamoxifen conjugate. The technology platform exploits conjugating antagonists and agonists and seeing their effects in various forms of diseases. In other words, the personalized technology platform may be designed on the basis of individual genetic make-up of cannabinoid receptors and estrogen receptors associated to each patient's disease. In other aspects, these synthesis methods may obviate the need of adding protecting groups to tamoxifen analogues and increase process efficiency and purify of the final product.

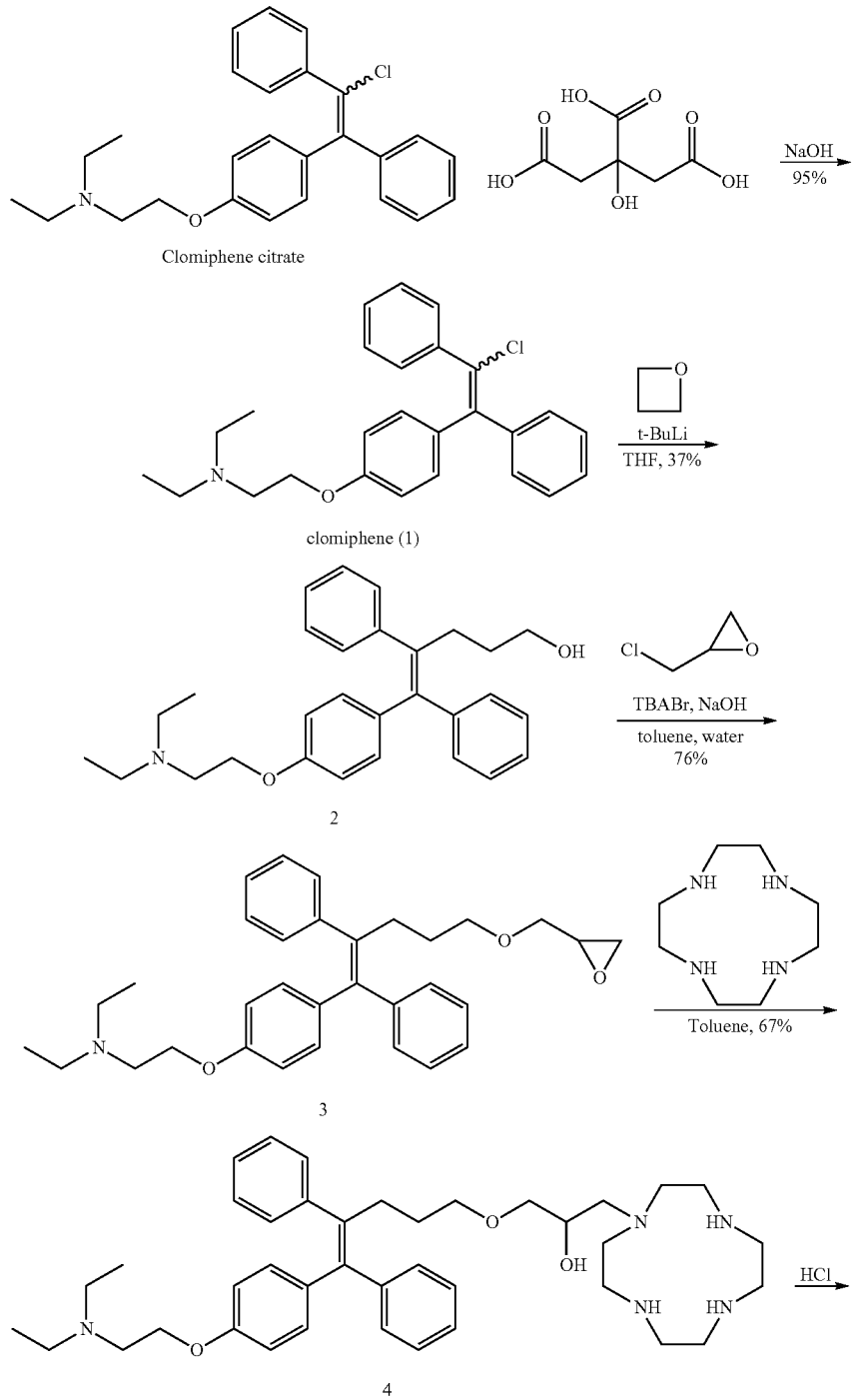

Scheme 2: Method of synthesizing Composition SC-05-K-1

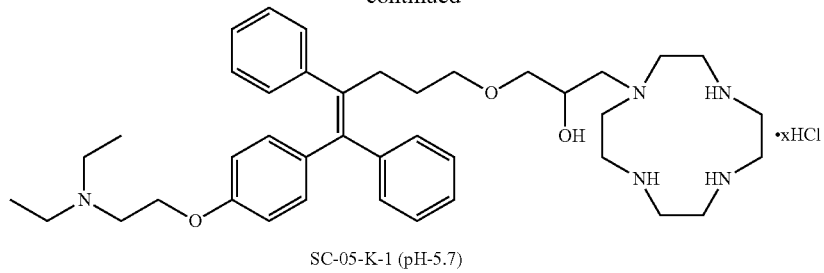
SC-05-K-1 (pH-5.7)
Scheme 3: Method of synthesizing Composition SC-05-L-1
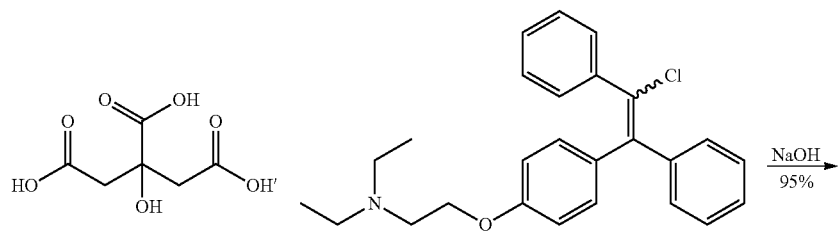
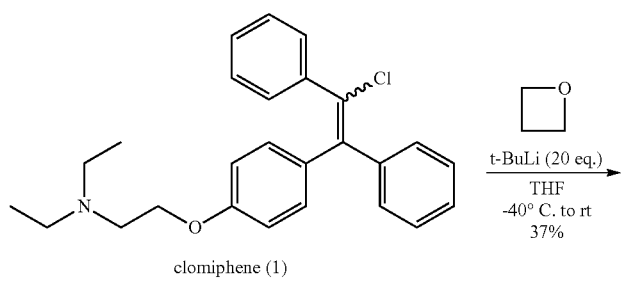
clomiphene (1)
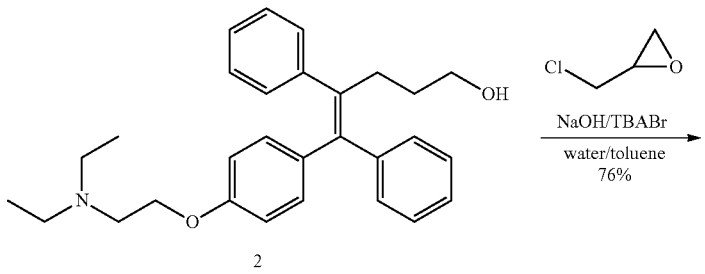
2
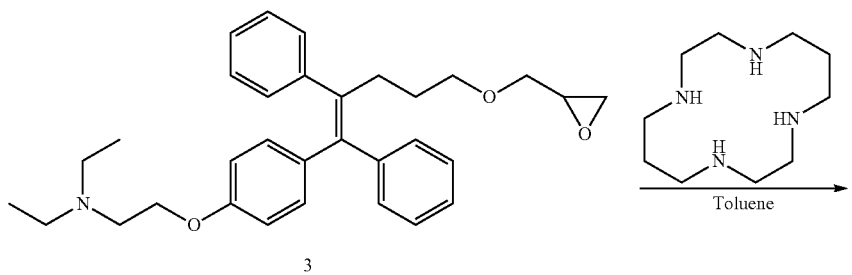
3

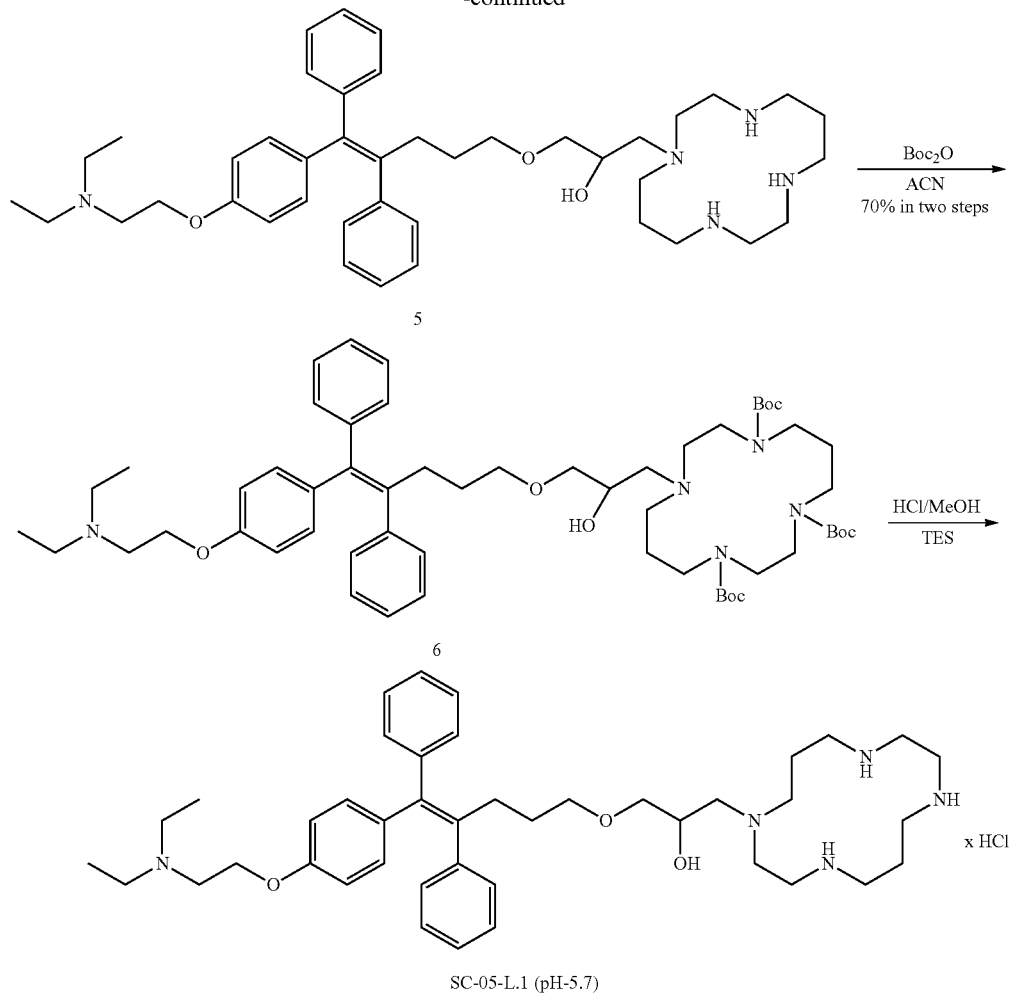

SC-05-L.1 (pH-5.7)

In addition, in some embodiments, pharmaceutical formulations or kits including the composition described above are provided. In other aspects, the composition may be further prepared in the pharmaceutical formulation or the kit using the chemical procedures known to skilled artisans. In some embodiments, the pharmaceutical formulation or the kit may further include antioxidants, stabilizing agents, preservatives or salts, for example. In some embodiments, the pharmaceutical formulation or the kit may include ascorbic acid, mannitol, tin (II) chloride and chelator-tamoxifen conjugate, for example. In some aspects, the pharmaceutical formulation or the kit may be an aqueous solution or a solution that has been frozen and/or lyophilized, for example. Herein, the "kit" is also called a "cold kit" in the field of molecular imaging.

Furthermore, the present invention accurately provides a method of imaging at the site of a disease in a given subject to perform a per/post treatment evaluation and to be able to monitor that subject for as long as that subject is being treated or under treatment with anti-estrogen. In certain aspects, the method includes detecting a signal generated by the radionuclide-labeled chelator-conjugates at the site of the disease of individual subjects, wherein a site of disease, if present, generates a signal that is more intense than surrounding the tissue. In some aspects, the metal ion may be a radionuclide and any radionuclide known to those of skill in art. In some embodiments, the radionuclides include $^{99m}$Tc, $^{67,68}$Ga, $^{60,61,62,64,67}$Cu, $^{111}$In, $^{166}$Ho, $^{186,188}$Re, $^{90}$Y, $^{177}$Lu, $^{223}$Ra, $^{225}$Ac, and $^{89}$Zr, $^{117m}$Sn, $^{153}$Sm, $^{89}$Sr, $^{59}$Fe, $^{212}$Bi, $^{211}$At, and $^{45}$Ti, for example, but the invention is not limited thereto. In other aspects, the metal ion may be a non-radioactive metal. In some embodiments, the site to be imaged may be a tumor or an ER-enriched tissue such as ovaries and uterine tissue. In some embodiments, the method may be defined as an imaging method for cancer, rheumatoid arthritis, osteoporosis, atherosclerosis, or endometrial tissue including administration of the composition described above. In one specific embodiment, the method may be defined as a method of imaging a site within a subject including detecting a signal from metal ion labeled chelator-receptor ligand conjugate that is localized at the site, but the invention is not limited thereto. In some embodiments, the signal may be detected using a technique selected from the group consisting of PET, PET/CT, SPECT, SPECT/CT, PET/MRI, SPECT/MRI, and an optical imaging hybrid with nuclear imaging device, for example. In other embodiments, the image may be a gamma image, a PET image, a PET/CT image, a SPECT image, a SPECT/CT image, a PET/MRI image, a SPECT/MRI image, or a hybrid image, for example. It should be noted that the composition described above may be made as a kit for imaging, and an imaging dose is defined as the kit. Besides, the method may be further defined as a method of treating a subject with cancer or endometriosis. In particular aspects, the cancer is breast cancer, lung cancer, prostate cancer, ovarian cancer, uterine cancer, cervical cancer, or endometrial cancer, for example, but the invention is not limited thereto. In some embodiments, the method may be defined as a treatment method for cancer, rheumatoid arthritis, osteoporosis, atherosclerosis, or endometrial tissue including administration of the composition described above, for example. In other words, there is provided a method of imaging a site, diagnosing a disease, or treating a disease within a subject including administering a metal ion labeled-chelator-receptor ligand conjugate to the subject, wherein the site is imaged, the disease is diagnosed, or the disease is treated.

On the other hand, it should be noted that the composition of the invention may be applied to molecular imaging and therapy. For example, the composition of the invention may be used as a molecular nuclear imaging agent. Specifically, the molecular nuclear imaging agent enables the comprehensive characterization of therapeutic intervention and can be used in patient selection, pharmacokinetic, dosage-finding and proof-of-concept studies. The effort in receptor image-guided cell therapy approaches in parallel with instrumentation development would be more comprehensive in the outcome assessment of patient response to treatment. More specifically, the molecular imaging agent using chelation provides advantages in batch-to-batch reproducibility of radiochemical yield, purity, production cost and the availability of the agent in routine clinical practice.

In addition, the invention technology platform integrates a metal ion, chelator, and receptor ligand. The receptor ligand may be used as a homing agent, which plays a dual role by cross talking between cell surface receptors and intracellular cytosolic receptors, thus, enhance cell uptake of the homing agent. For instance, CB1/CB2 receptor and ER pathways are overlapped in various cancers. Tamoxifen is known to provide cross-talk between ER and CBRs. Thus, it would be ideal to develop a tamoxifen-based imaging agent to measure ER systems activity via CB1/CB2 receptors. Such a tamoxifen-based imaging would help to monitor CB1/CB2 receptor and ER pathway-directed treatment response as well as predict the selection of patients for optimal treatment response. In this case, a hydroxy group was incorporated at the aliphatic spacers in chelator-tamoxifen conjugates to allow phosphorylation during diagnostic imaging with innovative tools to understand the dynamic changes in pathway-activated cell receptors leading to tissue degeneration, inflammatory, and proliferative disorders and to improve patient diagnosis, therapy and prognosis. However, the invention is not limited thereto.

To prove that the compositions of the present invention are suitable for imaging and be used for cancer therapy, the compositions of the present invention are synthesized and tested by using the method described in the following examples.

Example 1

Synthesis of Compound SC-05-K-1

In this example, 4 specific compounds (Compounds 1 to 4) and Compound SC-05-K-1 of the present invention were synthesized.

A. Synthesis of Compound 1

2N NaOH solution (10 mL) was added to a solution of clomiphene citrate (1 g, 1.69 mmol) and ethyl acetate (EA, 10 mL) at room temperature. The mixture was stirred vigorously for 30 min and extracted with EA three times (10 mL, 8 mL, 6 mL). The organic layer was concentrated under reduce pressure to give free-base clomiphene (Compound 1, 685.7 mg, 1.68 mmol, 99%) as a colorless oil.

B. Synthesis of Compound 2 tert-Butyl lithium (50 mL, 96 mmol, 1.9 M in pentane) was added drop wisely to a solution of Compound 1 (1.95 g, 4.8 mmol) in tetrahydrofuran (THF, 50 mL) at −40° C. Trimethylene oxide (6.26 mL, 96 mmol) was added drop wisely and the mixture was stirred at −40° C. for 30 min. The reaction was warmed to room temperature and stirred continuously at room temperature for 18 hr. Water was added to reaction carefully and the reaction was extracted with EA three times (50 mL, 30 mL, 20 mL). The EA layer was dried over anhydrous magnesium sulfate. After filtration, the EA solvent was concentrated under reduced pressure. The crude product was purified by column chromatography (EA/hexane/TEA, 1/3/0.1) to give (Z)-5-(4-(2-(diethylamino)ethoxy)phenyl)-4,5-diphenylpent-4-en-1-ol (Compound 2, 671.5 mg, 1.6 mmol, 36%) as a white solid.

C. Synthesis of Compound 3

To a suspension of Compound 2 (503.3 mg, 1.17 mmol) in 35% NaOH solution (12 mL), tetrabutyl ammonium bromide (TBABr, 113.3 mg, 0.35 mmol) was added. The reaction mixture was stirred vigorously. Epichlorohydrin (758.7 mg, 8.2 mmol) and few drops of toluene were then added to reaction. The reaction mixture was stirred at room temperature for 15 hr. EA (20 mL) was added to reaction and the reaction was extracted three times (15 mL, 10 mL). The organic layer was dried over magnesium sulfate. After filtration, the solvent was concentrated under reduced pressure and the crude product was purified by column chromatography (EA/hexane/TEA, 1/3/0.1) to give (Z)-N,N-diethyl-2-(4-(5-(oxiran-2-ylmethoxy)-1,2-diphenylpent-1-en-1-yl)phenoxy)ethan-1-amine (Compound 3, 432.1 mg, 0.89 mmol, 76%) as a yellow oil.

D. Synthesis of Compound 4

A mixture of 1,4,7,10-tetraazacyclododecane (cyclen, 642.9 mg, 3.73 mmol) and Compound 3 in toluene (4 mL) was heated to 100° C. until all the cyclen dissolved. The reaction mixture was stirred at 100° C. for 16 hr. The reaction was cooled to room temperature and kept in refrigerator for 3 hr. The precipitate of excess cyclen was then removed by filtration and washed with cold toluene. The toluene filtrates were combined and concentrated. The crude product was purified by column chromatography (DCM/MeOH/NH$_4$OH, 1/1/0.1) to give (Z)-1-(1,4,7,10-tetraazacyclododecan-1-yl)-3-((5-(4-(2-(diethylamino)ethoxy)phenyl)-4,5-diphenylpent-4-en-1-yl)oxy)propan-2-ol (Compound 4, 330 mg, 0.50 mmol, 67%) as a yellow oil.

E. Synthesis of Compound SC-05-K-1

1N HCl solution was added to a mixture of 4 (330 mg, 0.50 mmol) and water (1 mL) was added drop wisely until the pH value is 5-7. The mixture was then purified by reverse phase column chromatography to give pure Compound SC-05-K-1 (175 mg) as a white solid.

Characterization of Compounds 1-3 and Compound SC-05-K-1

NMR data was collected from 500 MHz Varian Inova NMR spectrometer (Palo Alto, Calif.) equipped with 5 mm PFG Triple $^1$H-$^{13}$C-$^{15}$N probe, 5 mm PFG $^1$H-$^{19}$C-$^{15}$N-$^{31}$P switchable probe and 4 mm $^1$H-$^{13}$C Nano probe. Mass Spectrometry was obtained from Bruker Solarix (Germany). HPLC data was collected from Waters 2695 Separations Module (Milford, Mass.) equipped with PC HILIC Column, (5 μm, 2.0 mm I.D.×150 mm).

Figure 1B:
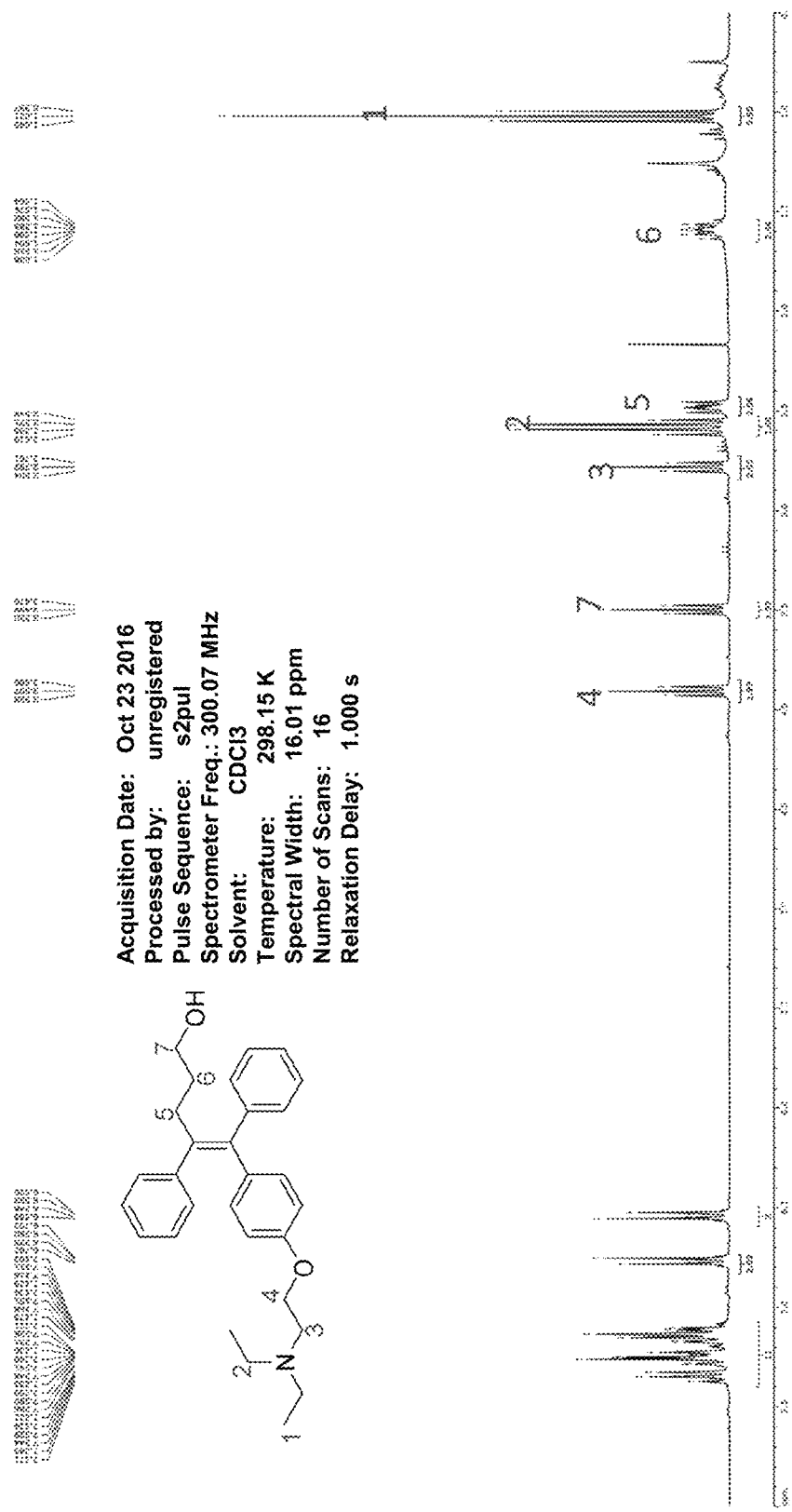
FIG. 1B shows the $^1$H-NMR spectrum of Compound 2 synthesized in Example 1 of the invention.
Figure 1C:
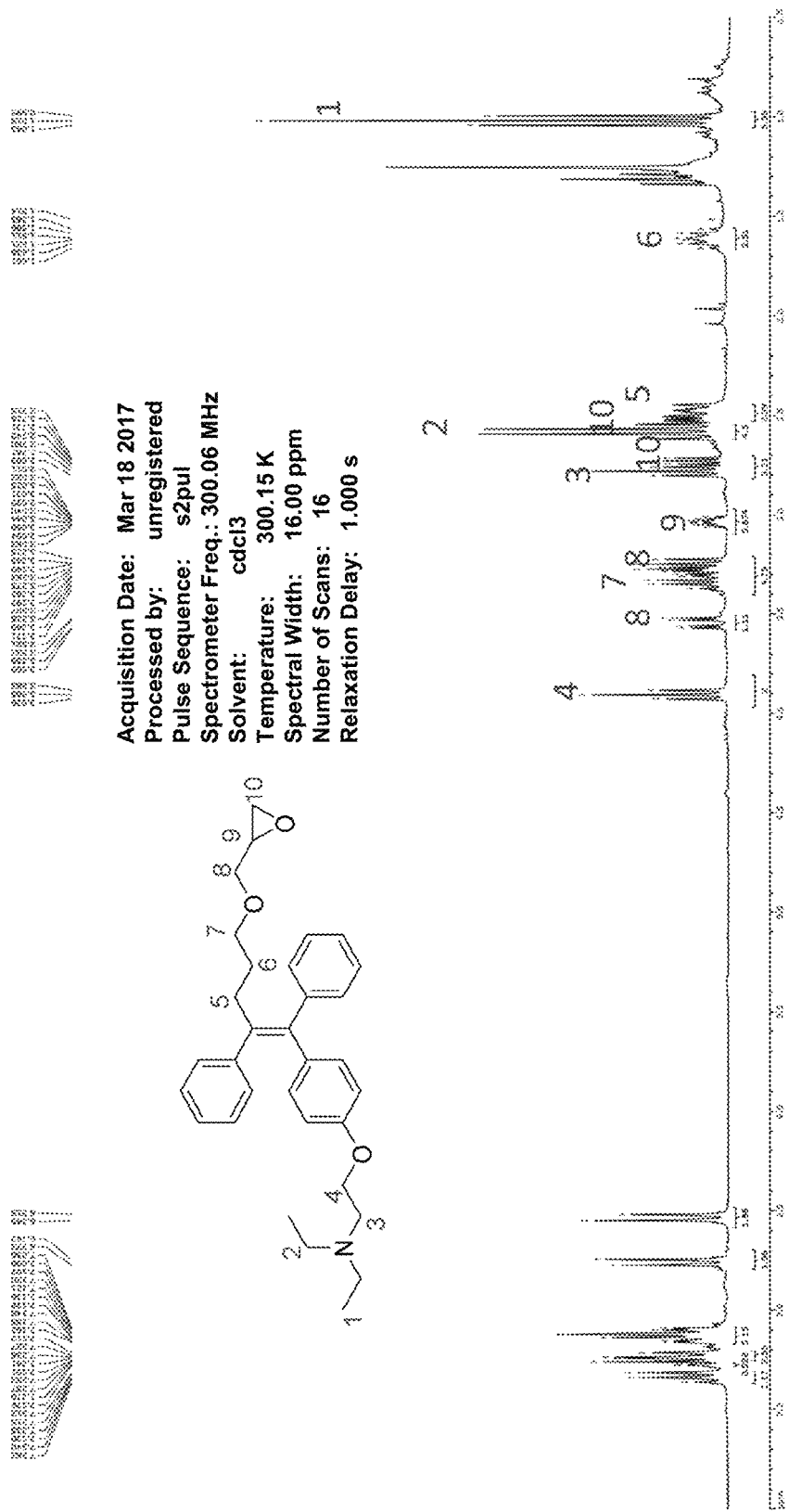
FIG. 1C shows the $^1$H-NMR spectrum of Compound 3 synthesized in Example 1 of the invention.

FIG. 1A shows the $^1$H-NMR spectrum of Compound 1 synthesized in Example 1 of the invention. FIG. 1B shows the $^1$H-NMR spectrum of Compound 2 synthesized in Example 1 of the invention. FIG. 1C shows the $^1$H-NMR spectrum of Compound 3 synthesized in Example 1 of the invention. The structures of Compounds 1-3 were confirmed by $^1$H-NMR, and the analysis results are presented in FIG. 1A to FIG. 1C respectively.

Figure 1D:
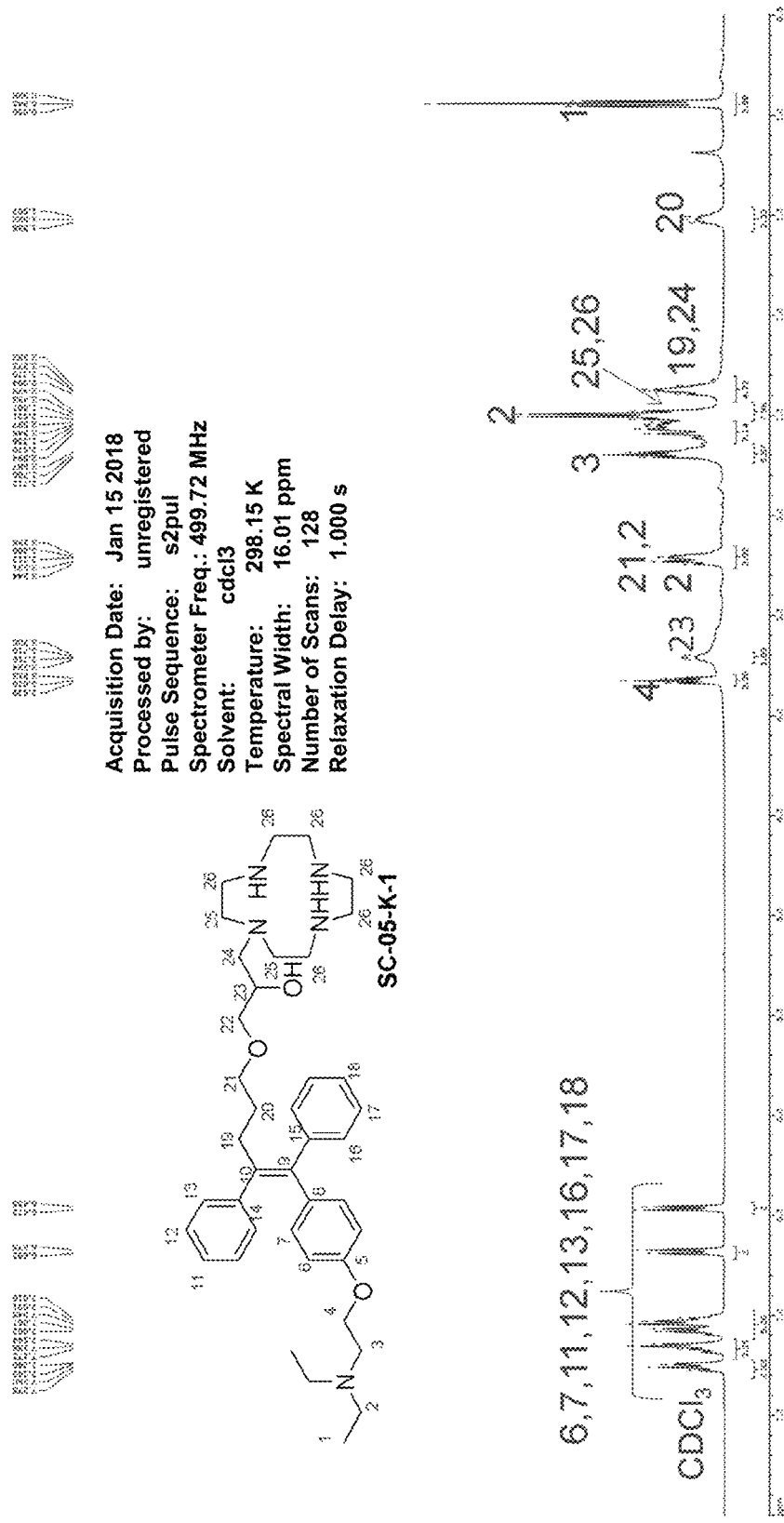
FIG. 1D shows the $^1$H-NMR spectrum of Compound SC-05-K-1 synthesized in Example 1 of the invention.
Figure 1E:
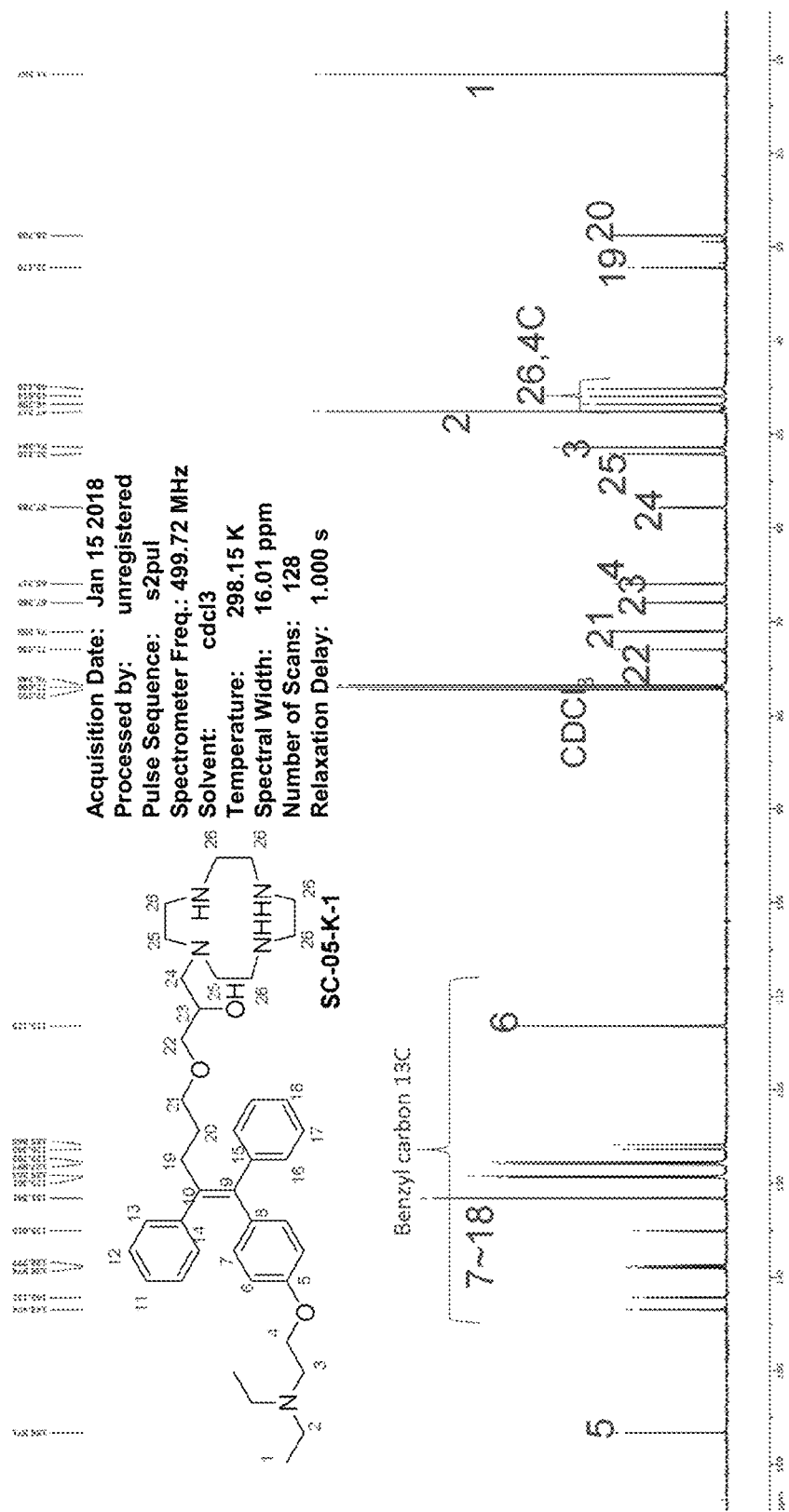
FIG. 1E shows the $^{13}$C-NMR spectrum of Compound SC-05-K-1 synthesized in Example 1 of the invention.
Figure 1F:
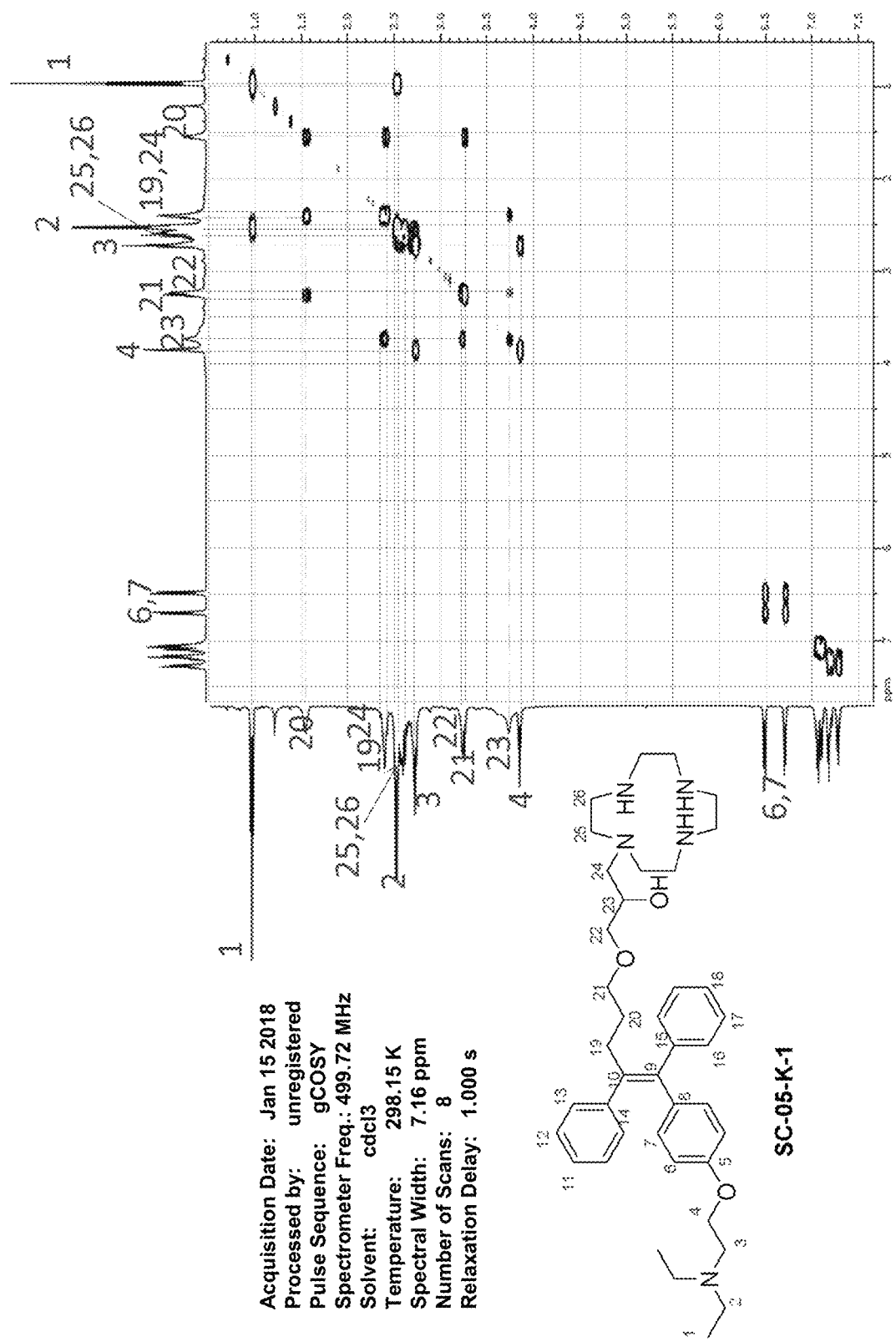
FIG. 1F shows the $^1$H-,$^1$H COSY NMR spectrum of Compound SC-05-K-1 synthesized in Example 1 of the invention.
Figure 1G:
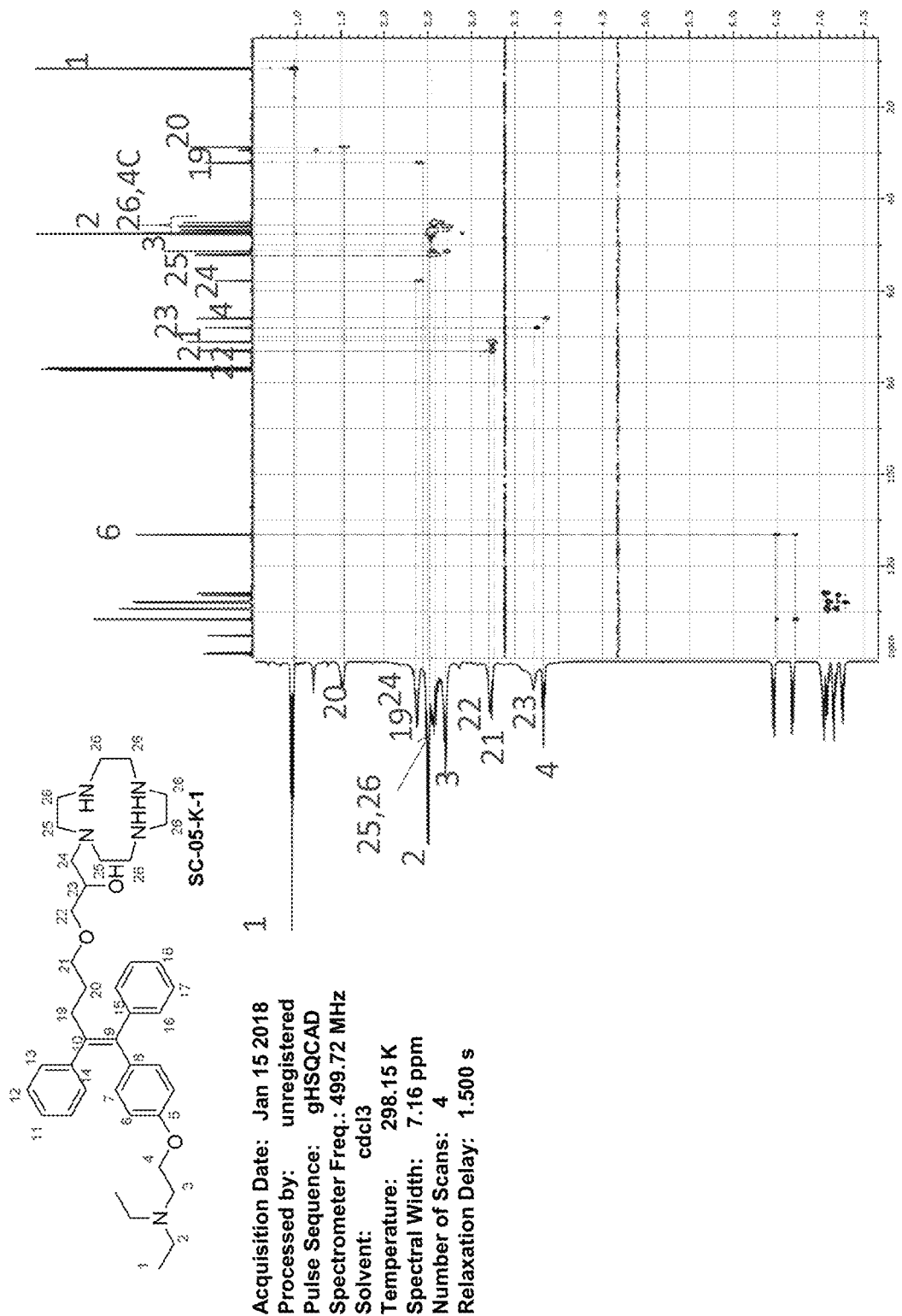
FIG. 1G shows the $^1$H-,$^{13}$C HSQC NMR spectrum of Compound SC-05-K-1 synthesized in Example 1 of the invention.
Figure 1H:
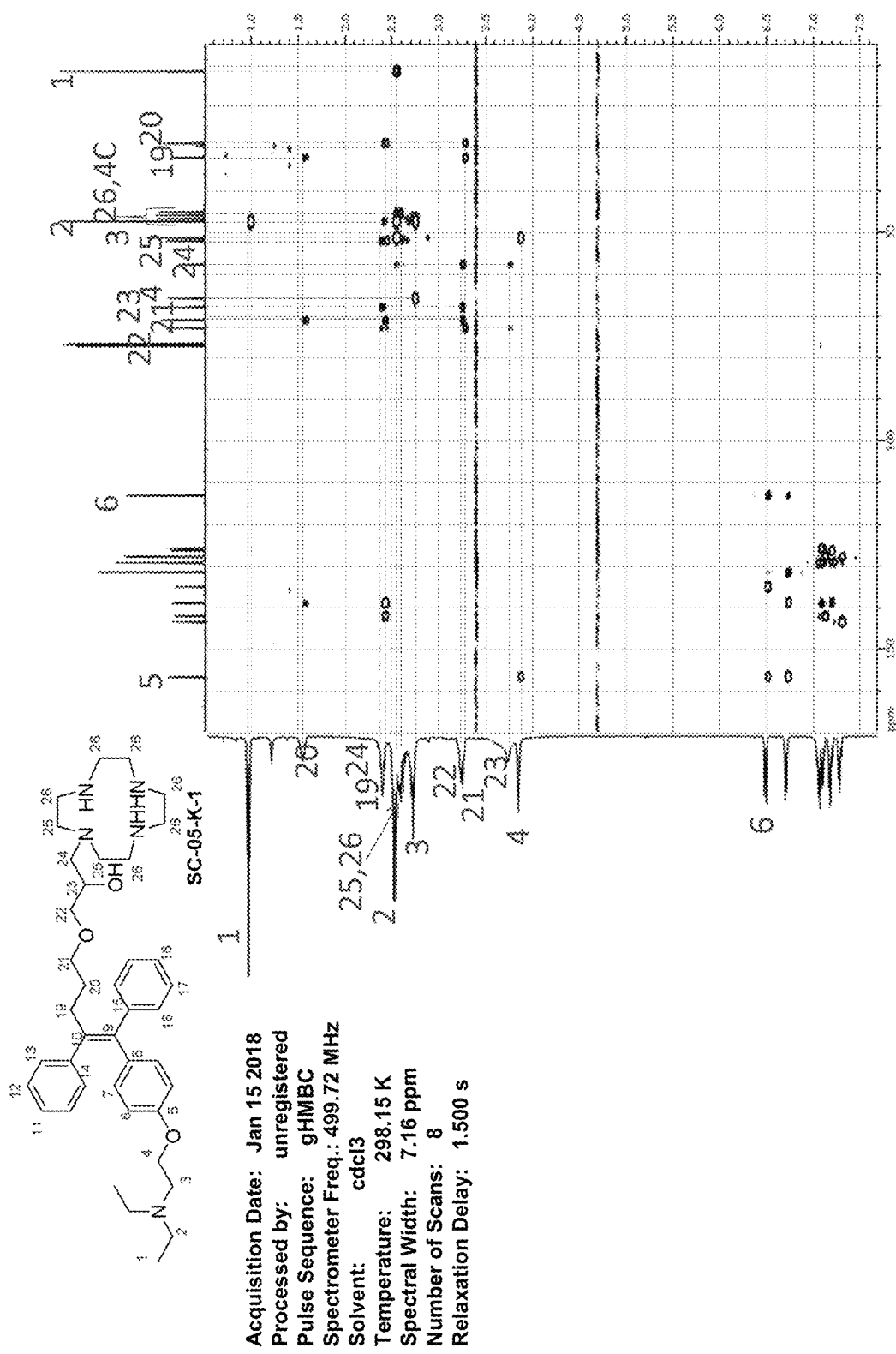
FIG. 1H shows the $^1$H-,$^{13}$C HMBC NMR spectrum of Compound SC-05-K-1 synthesized in Example 1 of the invention.
Figure 1I:
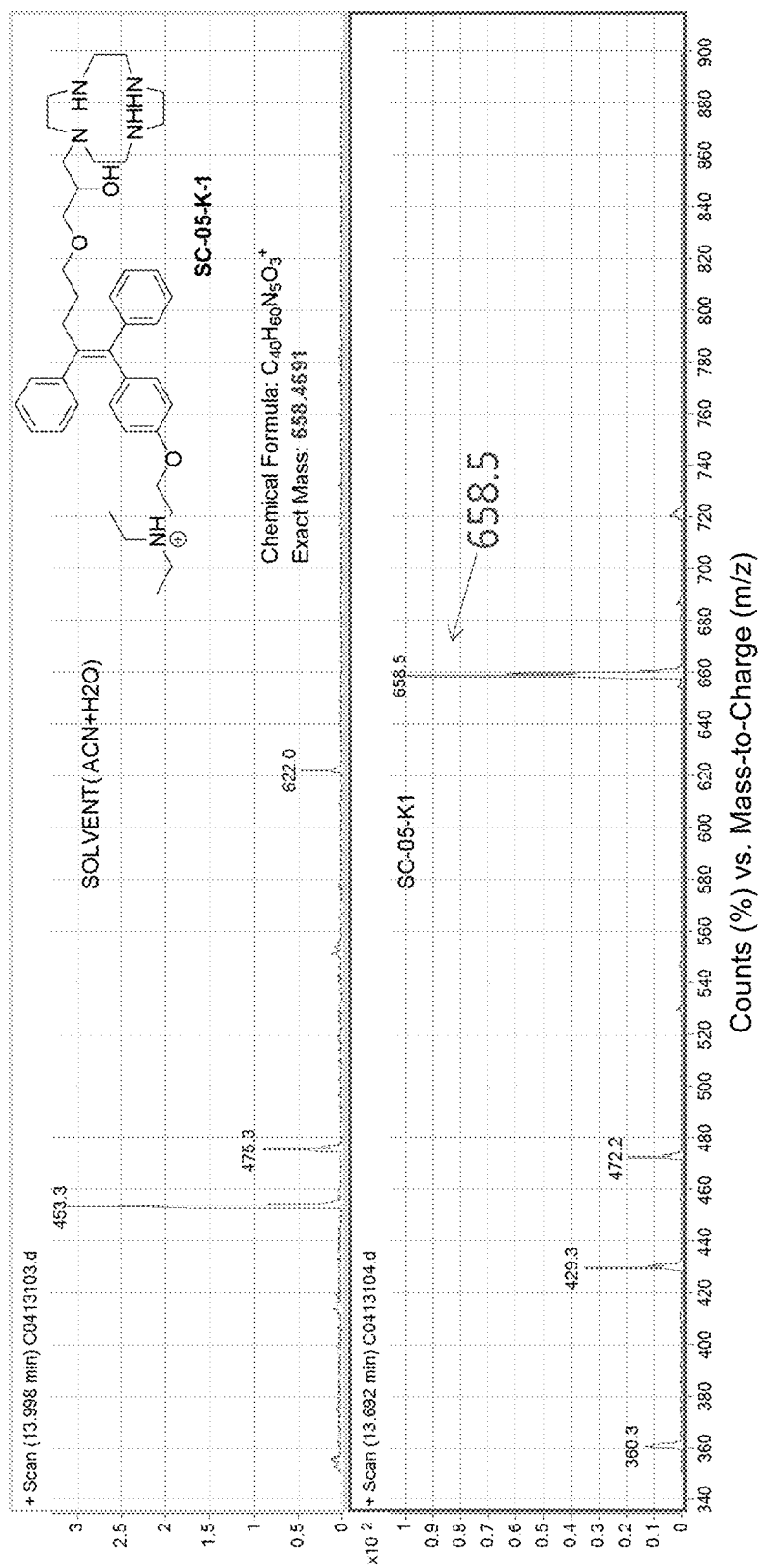
FIG. 1I shows the LC-MS spectrum of Compound SC-05-K-1 synthesized in Example 1 of the invention.
Figure 1J:
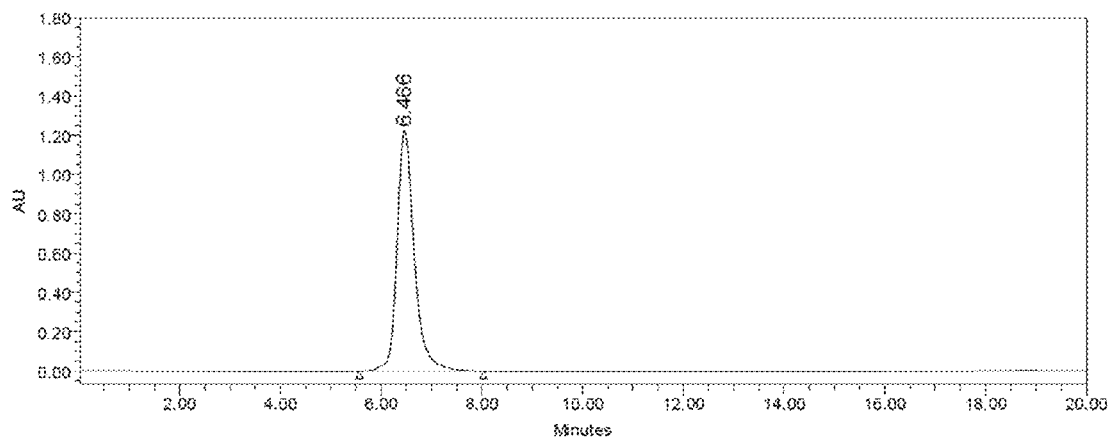
FIG. 1J shows the HPLC spectrum of Compound SC-05-K-1 synthesized in Example 1 of the invention.

FIG. 1D shows the $^1$H-NMR spectrum of Compound SC-05-K-1 synthesized in Example 1 of the invention. FIG. 1E shows the $^{13}$C-NMR spectrum of Compound SC-05-K-1 synthesized in Example 1 of the invention. FIG. 1F shows the $^1$H-,$^1$H COSY NMR spectrum of Compound SC-05-K-1 synthesized in Example 1 of the invention. FIG. 1G shows the $^1$H-,$^{13}$C HSQC NMR spectrum of Compound SC-05-K-1 synthesized in Example 1 of the invention. FIG. 1H shows the $^1$H-,$^{13}$C HMBC NMR spectrum of Compound SC-05-K-1 synthesized in Example 1 of the invention. FIG. 1I shows the LC-MS spectrum of Compound SC-05-K-1 synthesized in Example 1 of the invention. FIG. 1J shows the HPLC spectrum of Compound SC-05-K-1 synthesized in Example 1 of the invention. The structure of Compound SC-05-K-1 was confirmed by $^1$H-NMR, $^{13}$C-NMR, $^1$H-,$^1$H COSY NMR, $^1$H-,$^{13}$C HSQC NMR and $^1$H-,$^{13}$C HMBC NMR, and the analysis results are presented in FIG. 1D to FIG. 1H respectively. Also, Compound SC-05-K-1 was analyzed using mass spectrometry and the results are presented in FIG. 1I and FIG. 1J. As shown in FIG. 1J, HPLC analysis of Compound SC-05-K-1 (pH 5-7) using HILIC column shows the retention time around 6.5 min.

Example 2

Synthesis of Composition $^{99m}$Tc-SC-05-K-1

Sodium pertechnetate (Na$^{99m}$TcO$_4$) was obtained from $^{99}$Mo/$^{99m}$Tc generator by Covidien (Houston, Tex.). Radiosynthesis of Composition $^{99m}$Tc-SC-05-K-1 was achieved by adding $^{99m}$Tc-pertechnetate (40-50 mCi) into the lyophilized residue of Compound SC-05-K-1 (5 mg) and tin (II) chloride (SnCl$_2$, 100 μg). The complexation of Compound SC-05-K-1 with $^{99m}$Tc was carried out at pH 6.5.

Characterization of Composition $^{99m}$Tc-SC-05-K-1

Radiochemical purity was determined by TLC (Waterman No. 1, Aldrich-Sigma, St. Louis, Mo.) eluted with acetone and saline. High-performance liquid chromatography (HPLC), equipped with a NaI detector and UV detector (235 nm), was performed on a PC HILIC Column (2.0 mm I.D.×150 mm, Agilent, Santa Clara, Calif.) eluted with acetonitrile/water (1:1 V/V) at a flow rate of 0.5 mL/min.

Figure 1K:
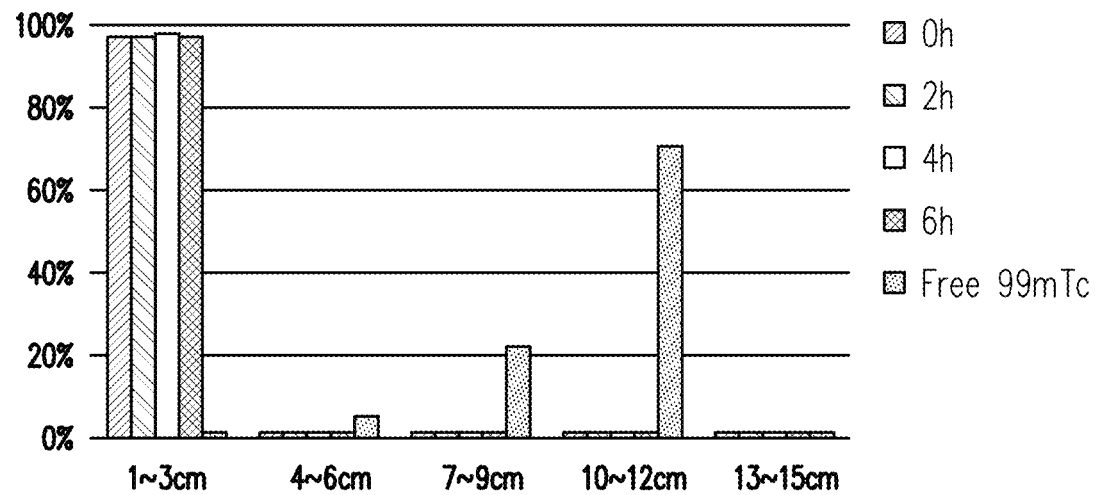
FIG. 1K and FIG. 1L show the radiochemical purity of Composition $^{99m}$Tc-SC-05-K-1 synthesized in Example 2 of the invention in two different systems.
Figure 1L:
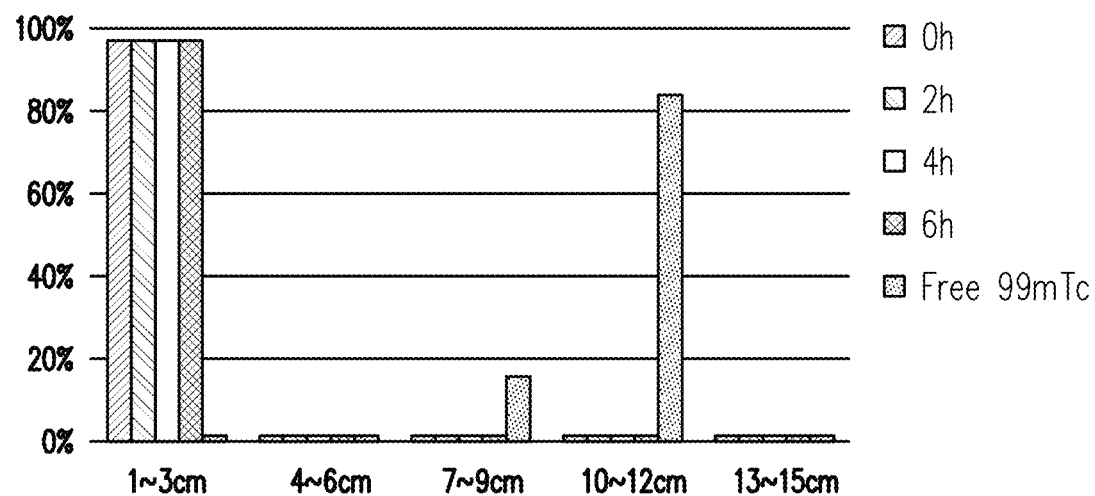

FIG. 1K and FIG. 1L show the radiochemical purity of Composition $^{99m}$Tc-SC-05-K-1 synthesized in Example 2 of the invention in two different systems. Specifically, FIG. 1K shows the radiochemical purity of Composition $^{99m}$Tc-SC-05-K-1 in an acetone system, and FIG. 1L shows the radiochemical purity of Composition $^{99m}$Tc-SC-05-K-1 in a saline system. As shown in FIG. 1K and FIG. 1L, the radiochemical purity of Composition $^{99m}$Tc-SC-05-K-1 (stayed at origin) was greater than 95% with Rf value 0.1 up to 6 hr, wherein free Na$^{99m}$TcO$_4$ was migrated to solvent front.

Figure 1M:
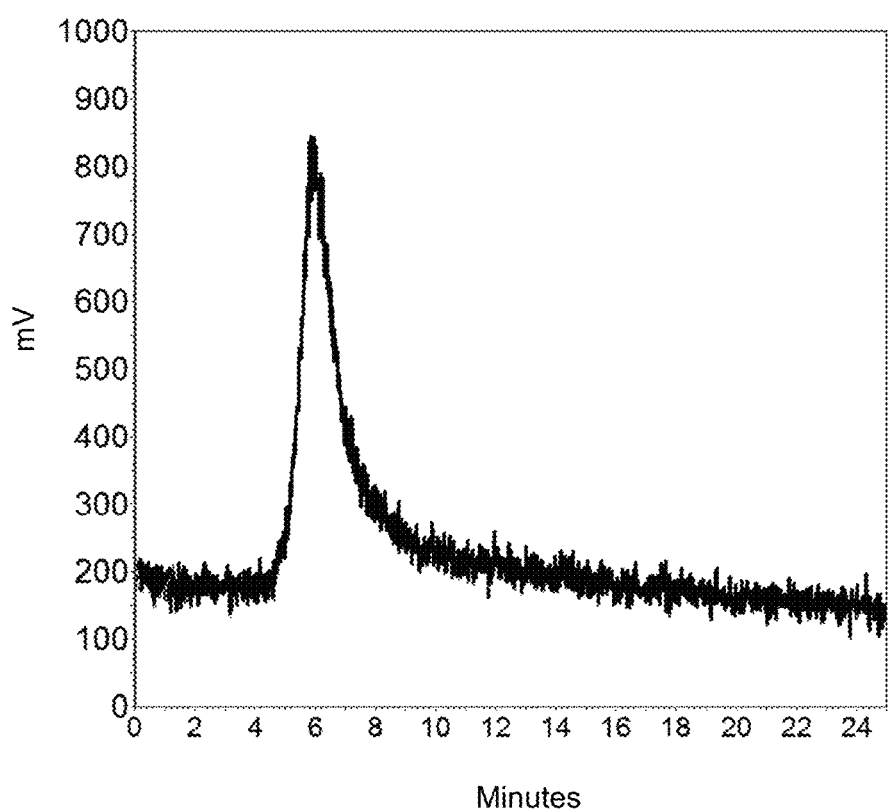
FIG. 1M shows the labeling efficiency of Composition $^{99m}$Tc-SC-05-K-1 synthesized in Example 2 of the invention.

FIG. 1M shows the labeling efficiency of Composition $^{99m}$Tc-SC-05-K-1 synthesized in Example 2 of the invention. Specifically, Composition SC-05-K-1 (5 mg in 100 μL saline) was added 100 μg tin (II) chloride (in 100 μL H$_2$O) followed by 200 μL Na$^{99m}$TcO$_4^-$ (~5 mCi). As shown in FIG. 1M, HPLC analysis of Composition $^{99m}$Tc-SC-05-K-1 shows the retention time around 6.5 min.

Example 3

Synthesis of Compound SC-05-L-1

In this example, 5 specific compounds (Compounds 1-3, 5 and 6) and Compound SC-05-L-1 of the present invention were synthesized. The synthesis of Compounds 1-3 are similar to that of Compounds 1-3 described above, and are not repeated herein.

F. Synthesis of Compound 5

To a round bottom flask, Compound 3 (500 mg, 1.0295 mmol), 1,4,8,11-tetraazacyclotetradecane (cyclam, 1040 mg, 5.140 mmol) were dissolved toluene (5 mL). Reaction solution was heated to 100° C. and refluxed overnight. The reaction mixture was then cooled to −20° C. The precipitate was removed by filtration and the filtrate was collected, dried over magnesium sulfate, filtered and the solvent was concentrated under vacuum to afford crude product (Z)-1-(1,4,8,11-tetraazacyclotetradecan-1-yl)-3-((5-(4-(2-(diethylamino)ethoxy)phenyl)-4,5-diphenylpent-4-en-1-yl)oxy)propan-2-ol (Compound 5). Compound 5 was directly used in next step without further purification.

G. Synthesis of Compound 6

To a suspension of Compound 5 (600 mg, 0.8746 mmol) in acetonitrile (10 mL), di-tert-butyl dicarbonate (1.53 g, 7.0103 mmol) was added drop wisely at room temperature. Reaction suspension was stirred overnight and gradually turn homogenous. As the reaction was completed, solution was concentrated under vacuum then purified by column chromatography with eluent hexane/ethylacetate/triethylamine=4/1/0.1 to give tri-tert-butyl (Z)-11-(3-((5-(4-(2-(diethylamino)ethoxy)phenyl)-4,5-diphenylpent-4-en-1-yl)oxy)-2-hydroxypropyl)-1,4,8,11-tetraazacyclotetradecane-1,4,8-tricarboxylate (Compound 6) as yellow sticky oil (two steps yield 70%).

H. Synthesis of Compound SC-05-L-1

To a round bottom flask of compound 5 (800 mg, 0.8111 mmol), triethylsilane (1.3 mL, 8.139 mmol) was added, followed by HCL (10 mL) in methanol (10 mL). Reaction solution was stirred at room temperature for 4 hr and monitored by TLC. As the reaction completed, solution was concentrated under vacuum, purified by reverse phase column chromatography with eluent from water to methanol to afford light yellow solid product (Z)-1-(1,4,8,11-tetraazacyclotetradecan-1-yl)-3-((5-(4-(2-(diethylamino)ethoxy)phenyl)-4,5-diphenylpent-4-en-1-yl)oxy)propan-2-ol hydrochloride salt (Compound SC-05-L-1, 637 mg).

Characterization of Compounds 5 and 6 and Compound SC-05-L-1

NMR data was collected from 500 MHz Varian Inova NMR spectrometer (Palo Alto, Calif.) equipped with 5 mm PFG Triple $^1$H-$^{13}$C-$^{15}$N probe, 5 mm PFG $^1$H-$^{19}$C-$^{15}$N-$^{31}$P switchable probe and 4 mm $^1$H-$^{13}$C Nano probe. Mass Spectrometry was obtained from Bruker Solarix (Germany). HPLC data was collected from Waters 2695 Separations Module (Milford, Mass.) equipped with PC HILIC Column, (5 μm, 2.0 mm I.D.×150 mm).

Figure 2A:
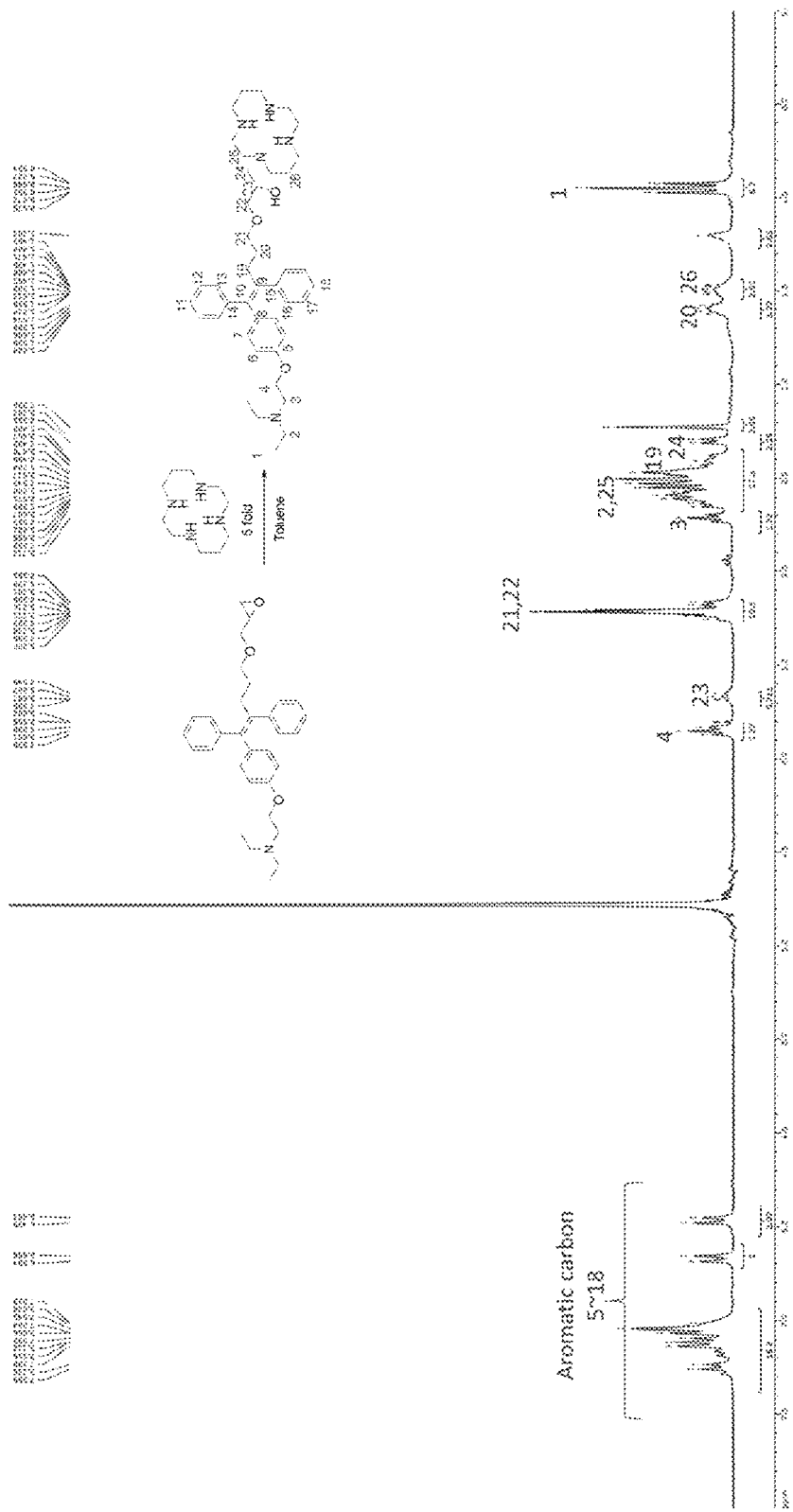
FIG. 2A shows the $^1$H-NMR spectrum of Compound 5 synthesized in Example 3 of the invention.
Figure 2B:
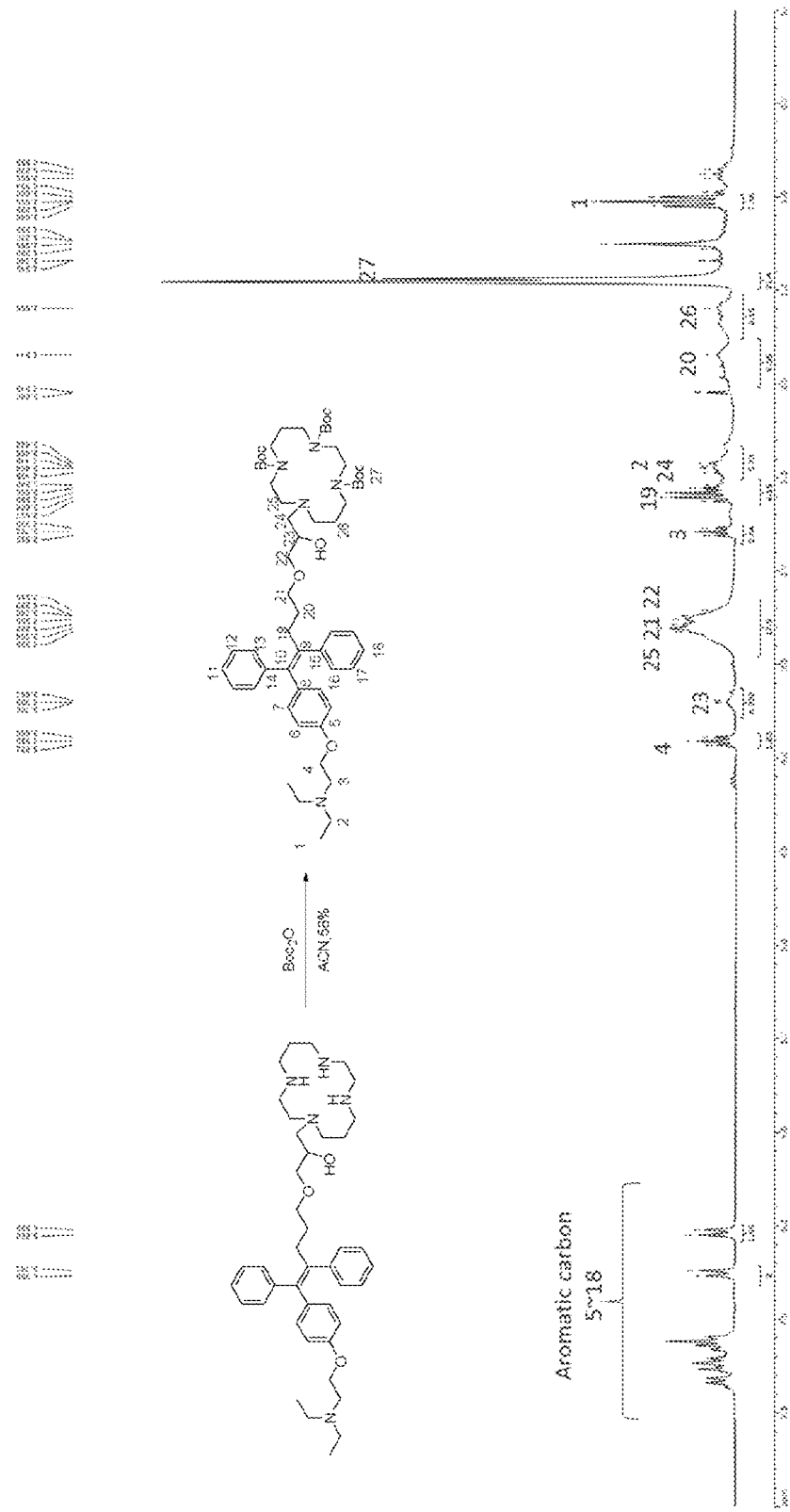
FIG. 2B shows the $^1$H-NMR spectrum of Compound 6 synthesized in Example 3 of the invention.

FIG. 2A shows the $^1$H-NMR spectrum of Compound 5 synthesized in Example 3 of the invention. FIG. 2B shows the $^1$H-NMR spectrum of Compound 6 synthesized in Example 3 of the invention. The structure of Compounds 5 and 6 were confirmed by $^1$H-NMR, and the analysis results are presented in FIG. 2A and FIG. 2B respectively.

Figure 2C:
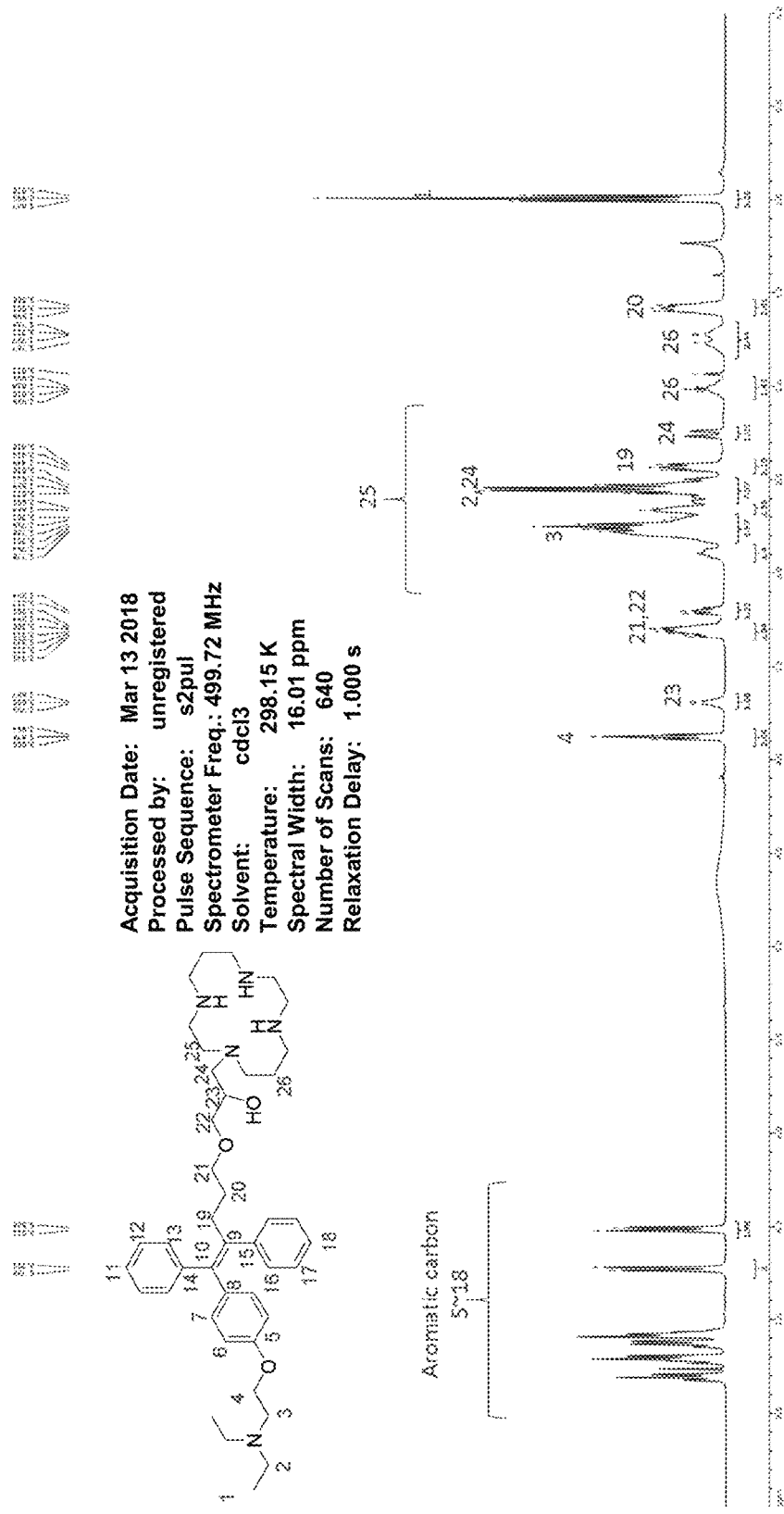
FIG. 2C shows the $^1$H-NMR spectrum of Compound SC-05-L-1 synthesized in Example 3 of the invention.
Figure 2D:
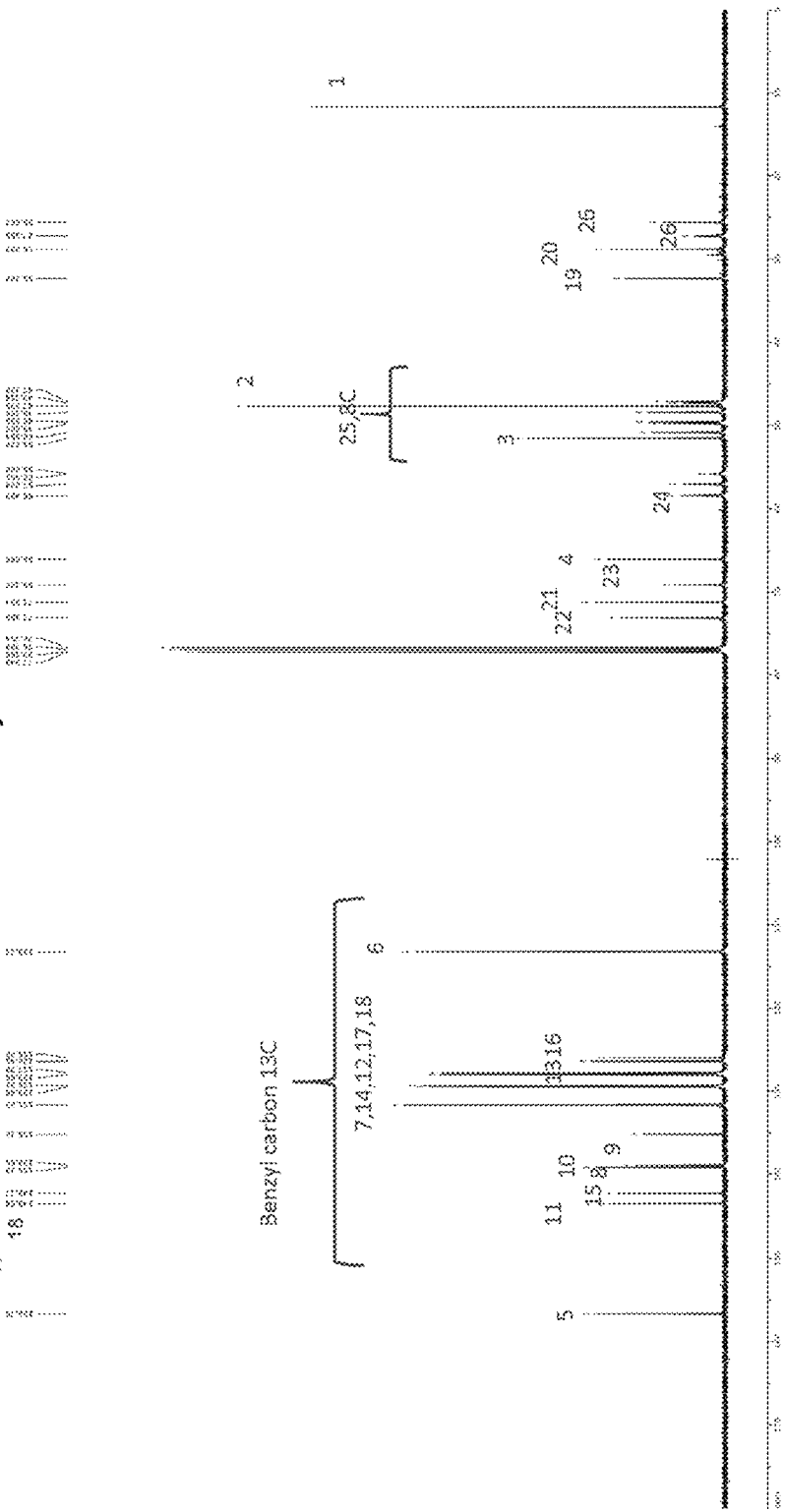
FIG. 2D shows the $^{13}$C-NMR spectrum of Compound SC-05-L-1 synthesized in Example 3 of the invention.
Figure 2E:
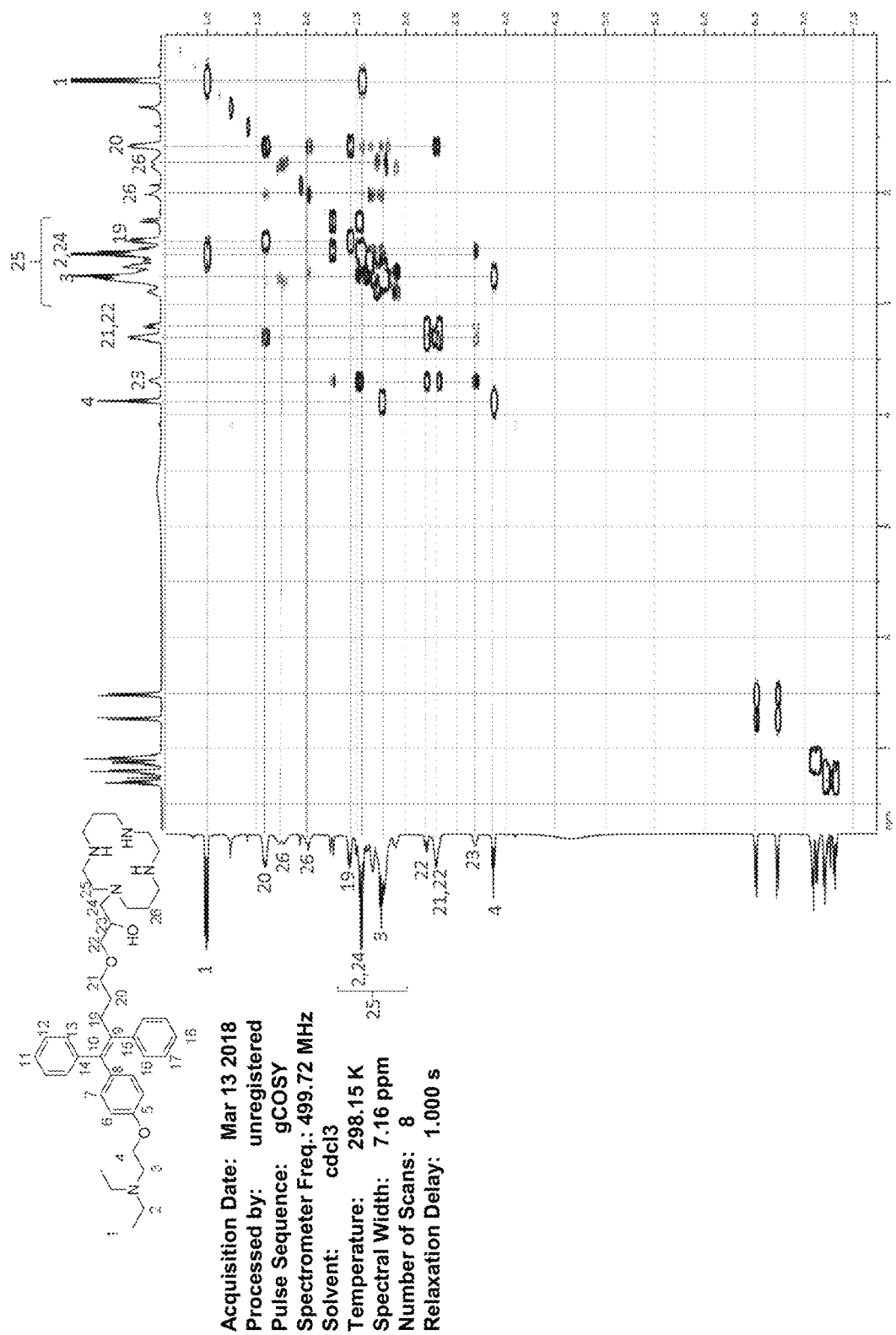
FIG. 2E shows the $^1$H-,$^1$H COSY NMR spectrum of Compound SC-05-L-1 synthesized in Example 3 of the invention.
Figure 2F:
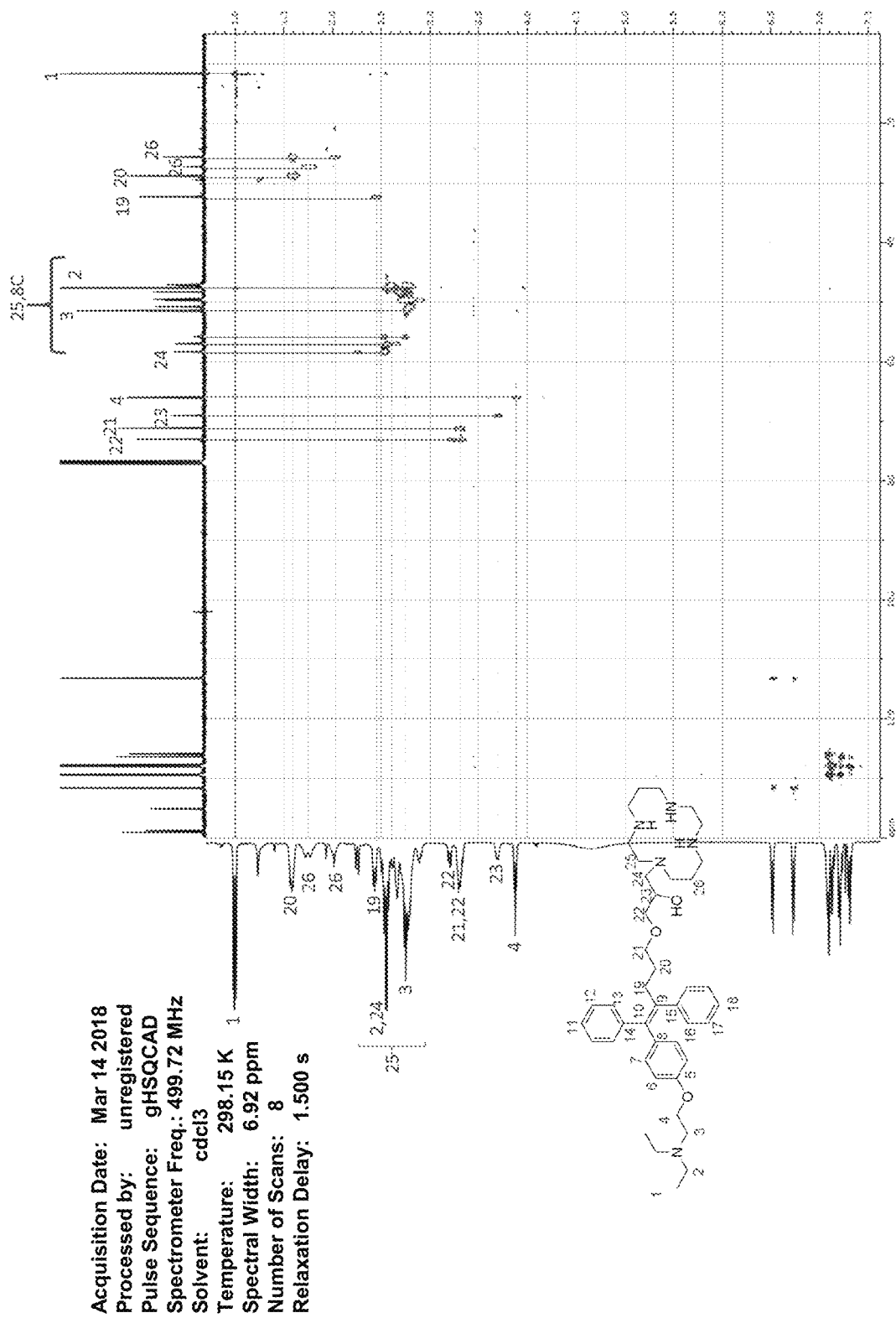
FIG. 2F shows the $^1$H-,$^{13}$C HSQC NMR spectrum of Compound SC-05-L-1 synthesized in Example 3 of the invention.
Figure 2G:
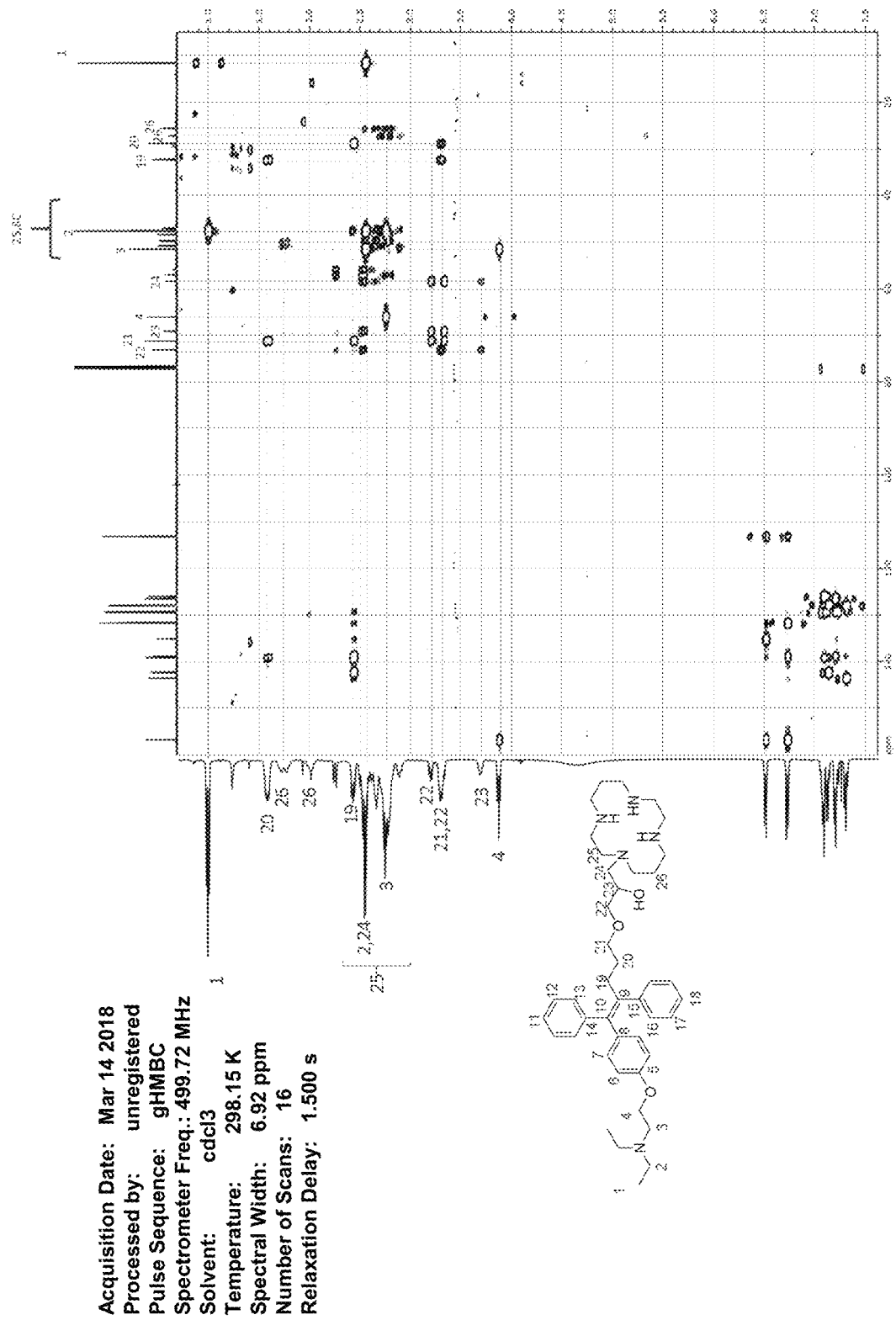
FIG. 2G shows the $^1$H-,$^{13}$C HMBC NMR spectrum of Compound SC-05-L-1 synthesized in Example 3 of the invention.
Figure 2H:
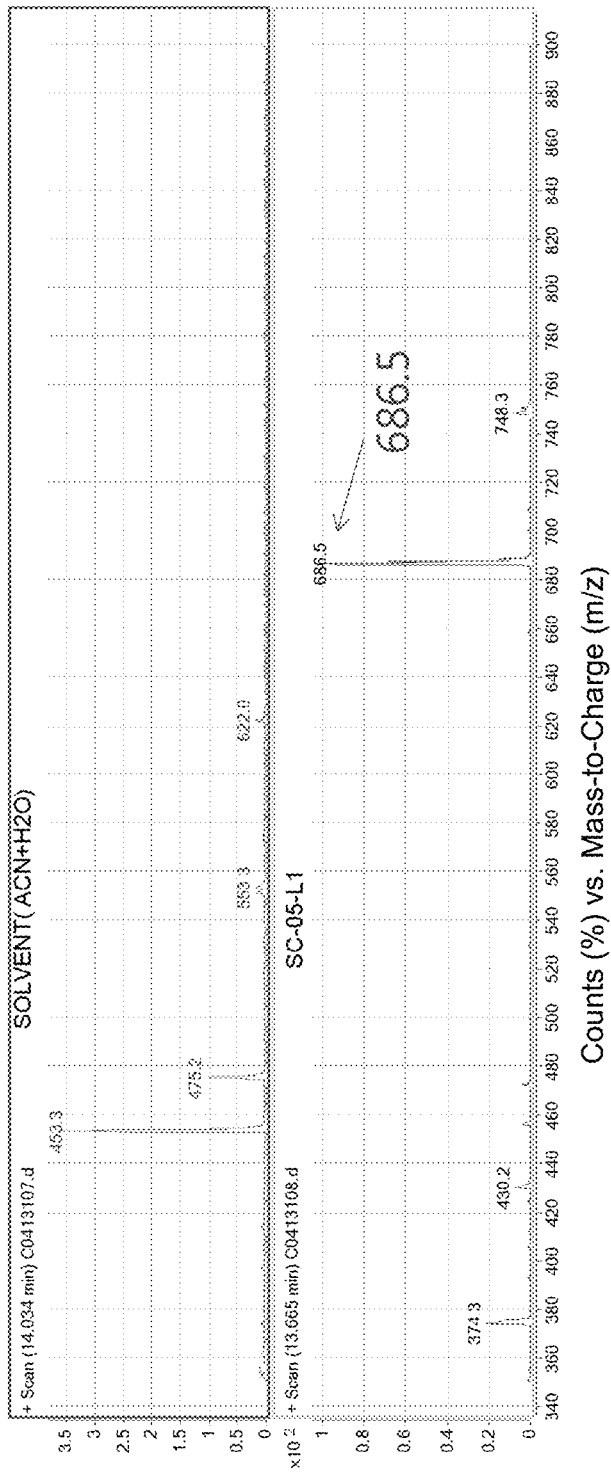
FIG. 2H shows the LC-MS spectrum of Compound SC-05-L-1 synthesized in Example 3 of the invention.
Figure 2I:
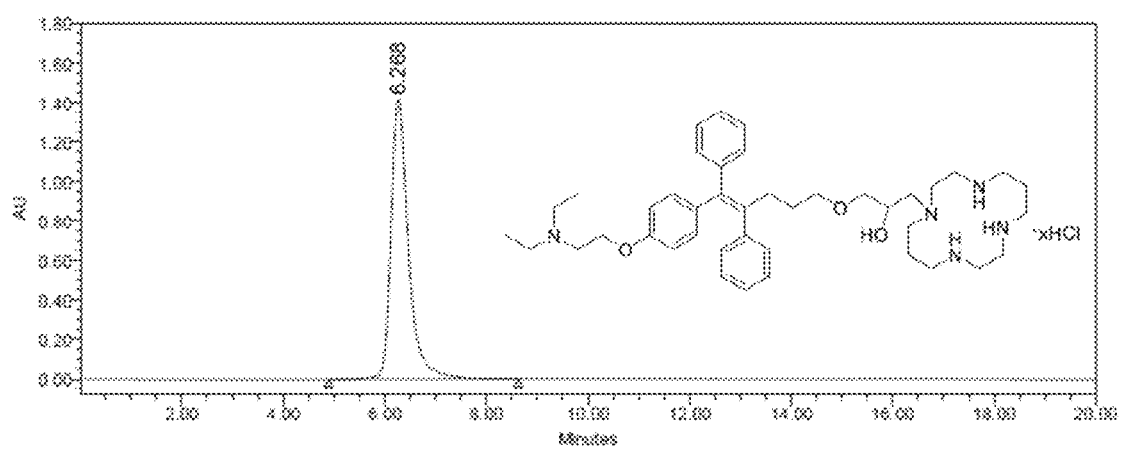
FIG. 2I shows the HPLC spectrum of Compound SC-05-L-1 synthesized in Example 3 of the invention.

FIG. 2C shows the $^1$H-NMR spectrum of Compound SC-05-L-1 synthesized in Example 3 of the invention. FIG. 2D shows the $^{13}$C-NMR spectrum of Compound SC-05-L-1 synthesized in Example 3 of the invention. FIG. 2E shows the $^1$H-,$^1$H COSY NMR spectrum of Compound SC-05-L-1 synthesized in Example 3 of the invention. FIG. 2F shows the $^1$H-,$^{13}$C HSQC NMR spectrum of Compound SC-05-L-1 synthesized in Example 3 of the invention. FIG. 2G shows the $^1$H-,$^{13}$C HMBC NMR spectrum of Compound SC-05-L-1 synthesized in Example 3 of the invention. FIG. 2H shows the LC-MS spectrum of Compound SC-05-L-1 synthesized in Example 3 of the invention. FIG. 2I shows the HPLC spectrum of Compound SC-05-L-1 synthesized in Example 3 of the invention. The structure of Compound SC-05-L-1 was confirmed by $^1$H-NMR, $^{13}$C-NMR, $^1$H-,$^1$H COSY NMR, $^1$H-,$^{13}$C HSQC NMR and $^1$H-,$^{13}$C HMBC NMR, and the analysis results are presented in FIG. 2C to FIG. 2G. Also, Compound SC-05-L-1 was analyzed using mass spectrometry and the results are presented in FIG. 2H and FIG. 2I. As shown in FIG. 2I, HPLC analysis of Compound SC-05-L-1 shows the retention time around 6.3 min.

Example 4

Synthesis of Composition $^{99m}$Tc-SC-05-L-1

Sodium pertechnetate (Na$^{99m}$TcO$_4$) was obtained from $^{99}$Mo/$^{99m}$Tc generator by Covidien (Houston, Tex.). Radiosynthesis of Composition $^{99m}$Tc-SC-05-L-1 was achieved by adding $^{99m}$Tc-pertechnetate (40-50 mCi) into the lyophilized residue of Compound SC-05-L-1 (5 mg) and tin (II) chloride (SnCl$_2$, 100 µg). The complexation of Compound SC-05-L-1 with $^{99m}$Tc was carried out at pH 6.5.

Characterization of Composition $^{99m}$Tc-SC-05-L-1

Radiochemical purity was determined by TLC (Waterman No. 1, Aldrich-Sigma, St. Louis, Mo.) eluted with acetone and saline. High-performance liquid chromatography (HPLC), equipped with a NaI detector and UV detector (280 nm), was performed on a PC HILIC Column (2.0 mm I.D.×150 mm, Agilent, Santa Clara, Calif.) eluted with acetonitrile/water (1:1 V/V) at a flow rate of 0.5 mL/min. Composition $^{99m}$Tc-SC-05-L-1 was sat at 24 hr for extended shelf-life stability assays.

Figure 2J:
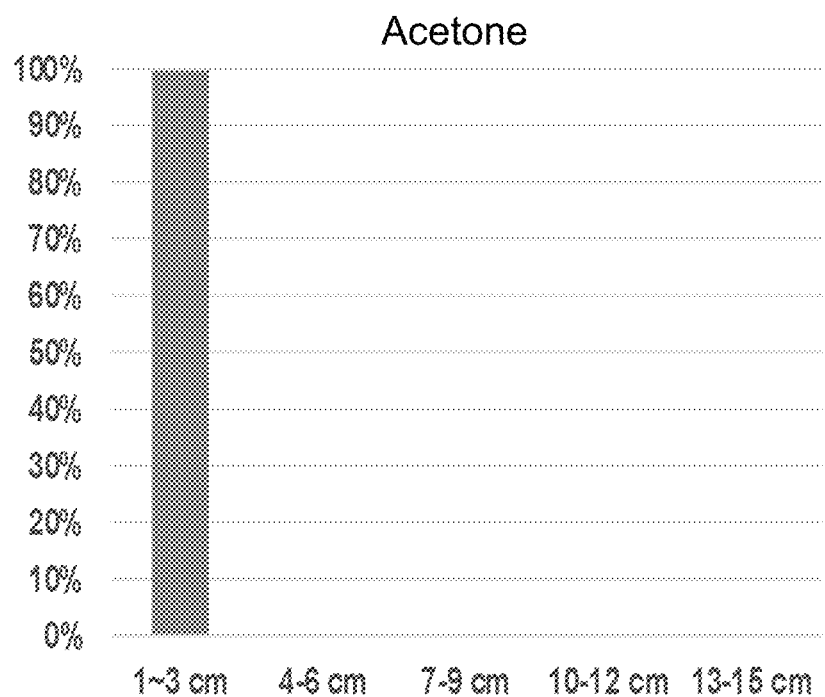
FIG. 2J and FIG. 2K show the radiochemical purity of Composition $^{99m}$Tc-SC-05-L-1 synthesized in Example 4 of the invention in two different systems.
Figure 2K:
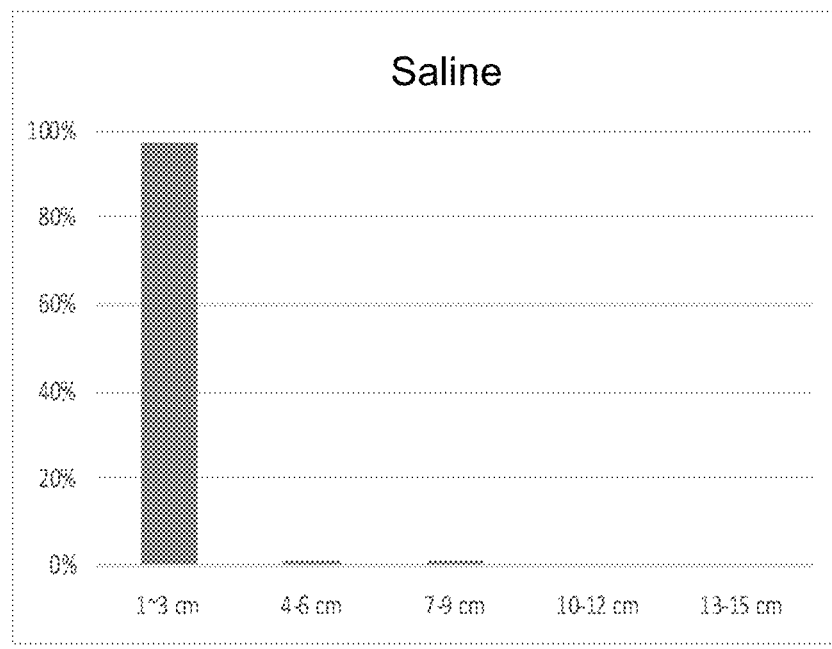

FIG. 2J and FIG. 2K show the radiochemical purity of Composition $^{99m}$Tc-SC-05-L-1 synthesized in Example 4 of the invention in two different systems. Specifically, FIG. 2J shows the radiochemical purity of Composition $^{99m}$Tc-SC-05-L-1 in an acetone system, and FIG. 2K shows the radiochemical purity of Composition $^{99m}$Tc-SC-05-L-1 in a saline system. As shown in FIG. 2J and FIG. 2K, the radiochemical purity of Composition $^{99m}$Tc-SC-05-L-1 was greater than 95% with Rf value 0.1.

Figure 2L:
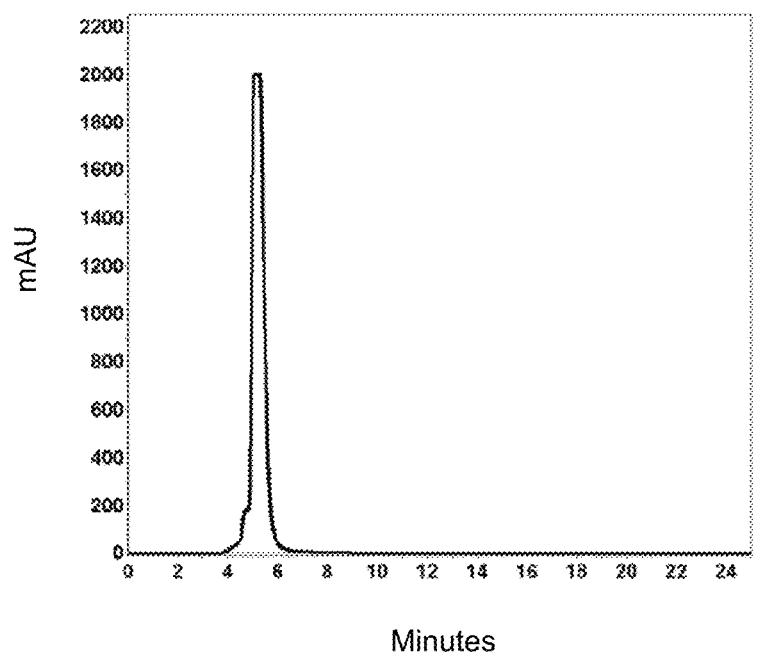
FIG. 2L and FIG. 2M show the labeling efficiency of Composition $^{99m}$Tc-SC-05-L-1 synthesized in Example 4 of the invention in two different systems.
Figure 2M:
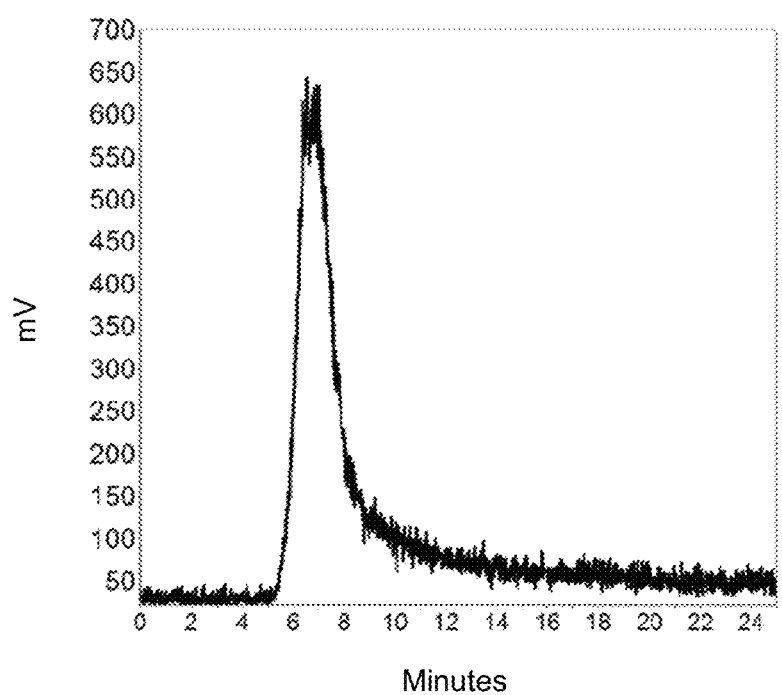

FIG. 2L and FIG. 2M show the labeling efficiency of Composition $^{99m}$Tc-SC-05-L-1 synthesized in Example 4 of the invention in two different systems. Specifically, Composition SC-05-L-1 (5 mg in 100 µL saline) was added 100 µg tin (II) chloride (in 100 µL H$_2$O) followed by 200 µL Na$^{99m}$TcO$_4^-$ (~5 mCi). As shown in FIG. 2L (280 nm channel) and FIG. 2M (radiostar channel), HPLC analysis of Composition $^{99m}$Tc-SC-05-L-1 shows the retention time around 7 min.

Figure 2N:
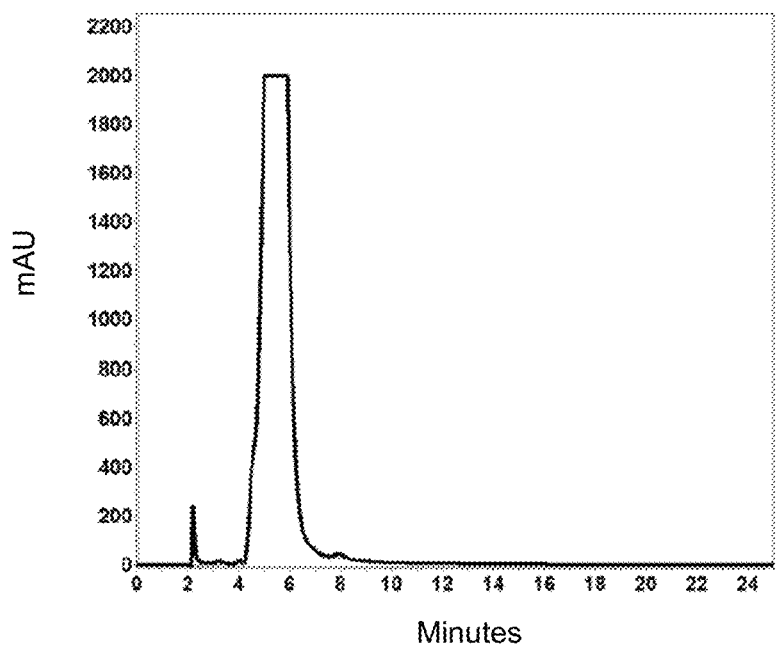
FIG. 2N and FIG. 2O show the in vitro stability of Composition $^{99m}$Tc-SC-05-L-1 synthesized in Embodiment 2 of the invention in two different systems.
Figure 2O:
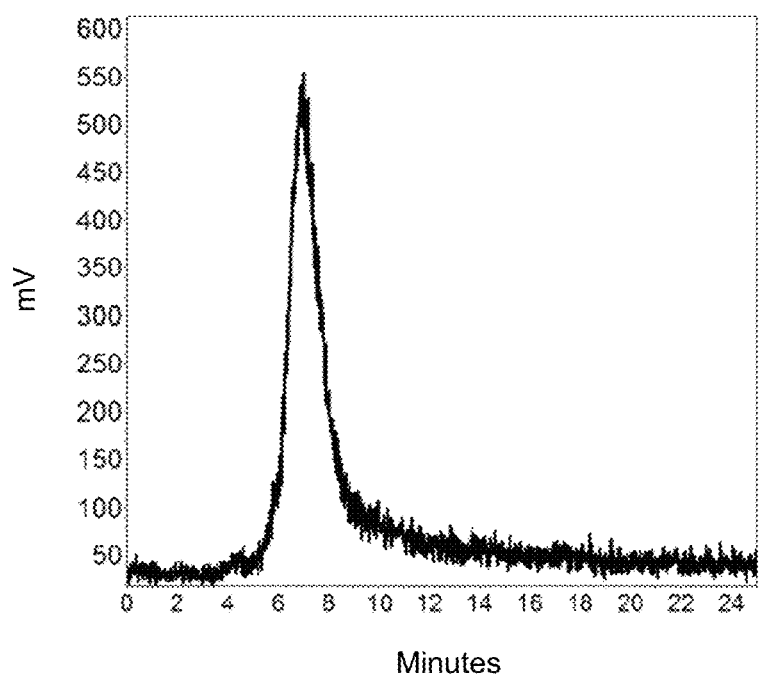

FIG. 2N and FIG. 2O show the in vitro stability of Composition $^{99m}$Tc-SC-05-L-1 synthesized in Example 4 of the invention in two different systems. Specifically, the in vitro stability of Composition $^{99m}$Tc-SC-05-L-1 was measured after incubation at room temperature for 24 hr. As shown in FIG. 2N (280 nm channel) and FIG. 2O (radiostar channel), Composition $^{99m}$Tc-SC-05-L-1 was stable in pH 6.5 after 24 hr.

Example 5

In Vitro Cellular Uptake Studies

Experiment 1

Compound SC-05-K-1 and Compound SC-05-L-1 (5 mg each) were dissolved in 0.3 mL water at pH 5-6. SnCL$_2$ (0.1 mg in 0.1 mL) was added (prepared from 10 mg tin (II) in 10 mL water), then Na$^{99m}$TcO$_4$ (5 mCi in 0.1 mL) was added. The total volume was diluted with water to 1 mL. The cell uptake for each well was 5 mg/5 mCi/1 mL (0.1 mg/0.1 mCi/20 uL/well). Each well contained 10 µg molecule. Multi-cell lines were used for cell uptake assays. A 96-well plate was used for MCF-7 ER(+) cell uptake studies. Each well contained 200,000 MCF-7 cells in 150 µL serum free RPMI. Composition $^{99m}$Tc-SC-05-K-1 and Composition $^{99m}$Tc-SC-05-L-1 were added to each well containing cells in the culture medium for different intervals (1-4 hr). To ascertain the cell uptake was via ER mediated process, Estradiol (10-100 times) was added to the MCF-7 cells. The cell uptake was expressed as percent of total dose.

FIG. 3A and FIG. 3B show the MCF-7 cell uptake and blocking studies of Composition $^{99m}$Tc-SC-05-K-1 and Composition $^{99m}$Tc-SC-05-L-1 synthesized in Example 2 and Example 4 of the invention. As shown in FIG. 3A and FIG. 3B, both Composition $^{99m}$Tc-SC-05-K-1 and Composition $^{99m}$Tc-SC-05-L-1 showed good cell uptake. Particularly, cell uptake was decreased (30-40%) after adding estradiol in Composition $^{99m}$Tc-SC-05-L-1 as shown in FIG. 3A.

Experiment 2

A 6-well plate was used for OVCAR3 ER(+) and TOV-112D ER(−) cell uptake studies. Each well contained 100,000 cells in 150 µL serum free RPMI. Composition $^{99m}$Tc-SC-05-K-1 and Composition $^{99m}$Tc-SC-05-L-1 were added to each well containing cells in the culture medium for different intervals (0-2 hr). To ascertain OVCAR3 cell uptake of Composition $^{99m}$Tc-SC-05-L-1 was via an ER mediated process, a blocking study was conducted. For blocking study, the amount of estrone used was 1 µg/well which was 1% of Composition $^{99m}$TC-SC-05-L-1 dose (0.1 mg/0.1 mCi/20 µL/well). The well containing cells in the culture medium was incubated for different intervals (0-2 hr). Subsequently, cells are washed with ice-cold phosphate-buffered saline PBS twice and trypsinized with 0.5 mL of trypsin solution to detach tumor cells. Protein concentration assay was used to determine the proteins in each well. The cells were lysed in the lysis buffer containing proteinase inhibitors (Roche Diagnostic, Mannheim, Germany). The protein concentration in the cell lysate was quantified using Bradford Method as described by the manufacture (Bio-RAD, Hercules, Calif., USA). The Bradford dye was diluted in distilled water (1:4) and filtered through filter paper (number 1, Whatman no. 1, Advantec Co. Ltd., Tokyo). Bovine serum albumin at the concentration of 1000 µg/ml, 500 µg/ml, 250 µg/ml, 125 µg/ml, 62.5 µg/ml, 31.25 µg/ml were used to build a standard curve. Protein samples were diluted in lysis buffer at 1:9. Diluted protein samples or standard were mixed with Bradford dye in 96 well, then the absorbance at 595 nm was recorded. The radioactivity concentration in the cells and culture medium was measured with a gamma counter (Packard, Conn.) and expressed as cpm/g of cells and cpm/g medium. The protein mass-to-medium radioactivity concentration ratio was calculated and plotted over time.

Figure 4A:
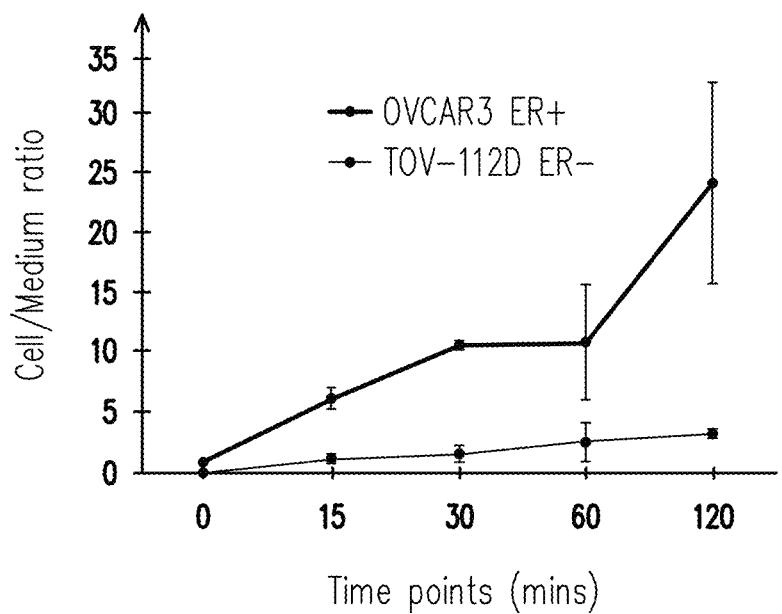
FIG. 4A and FIG. 4B show the OVCAR3 cell and TOV-112D cell uptake studies of Composition $^{99m}$Tc-SC-05-K-1 and Composition $^{99m}$Tc-SC-05-L-1 synthesized in Example 2 and Example 4 of the invention.
Figure 4B:
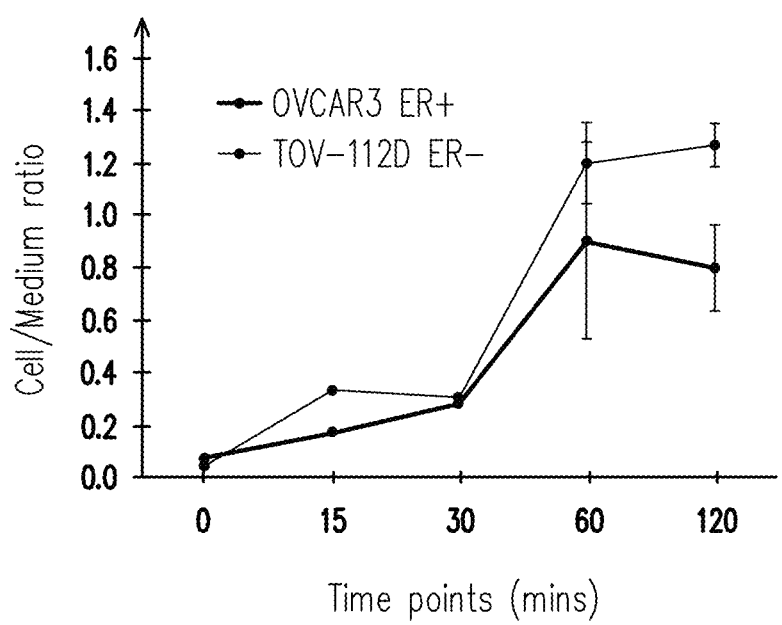

FIG. 4A and FIG. 4B show the OVCAR3 cell and TOV-112D cell uptake studies of Composition $^{99m}$Tc-SC-05-K-1 and Composition $^{99m}$Tc-SC-05-L-1 synthesized in Example 2 and Example 4 of the invention. As shown in FIG. 4A and FIG. 4B, cell uptake studies with Composition $^{99m}$Tc-SC-05-L-1 and Composition $^{99m}$Tc-SC-05-K-1 indicated that Composition $^{99m}$Tc-SC-05-L-1 had higher uptake in ER(+) OVCAR3 cells than ER(−) TOV-112D cells. Also, Composition $^{99m}$Tc-SC-05-L-1 had higher cell/media ratios than Composition $^{99m}$Tc-SC-05-K-1.

Figure 5:
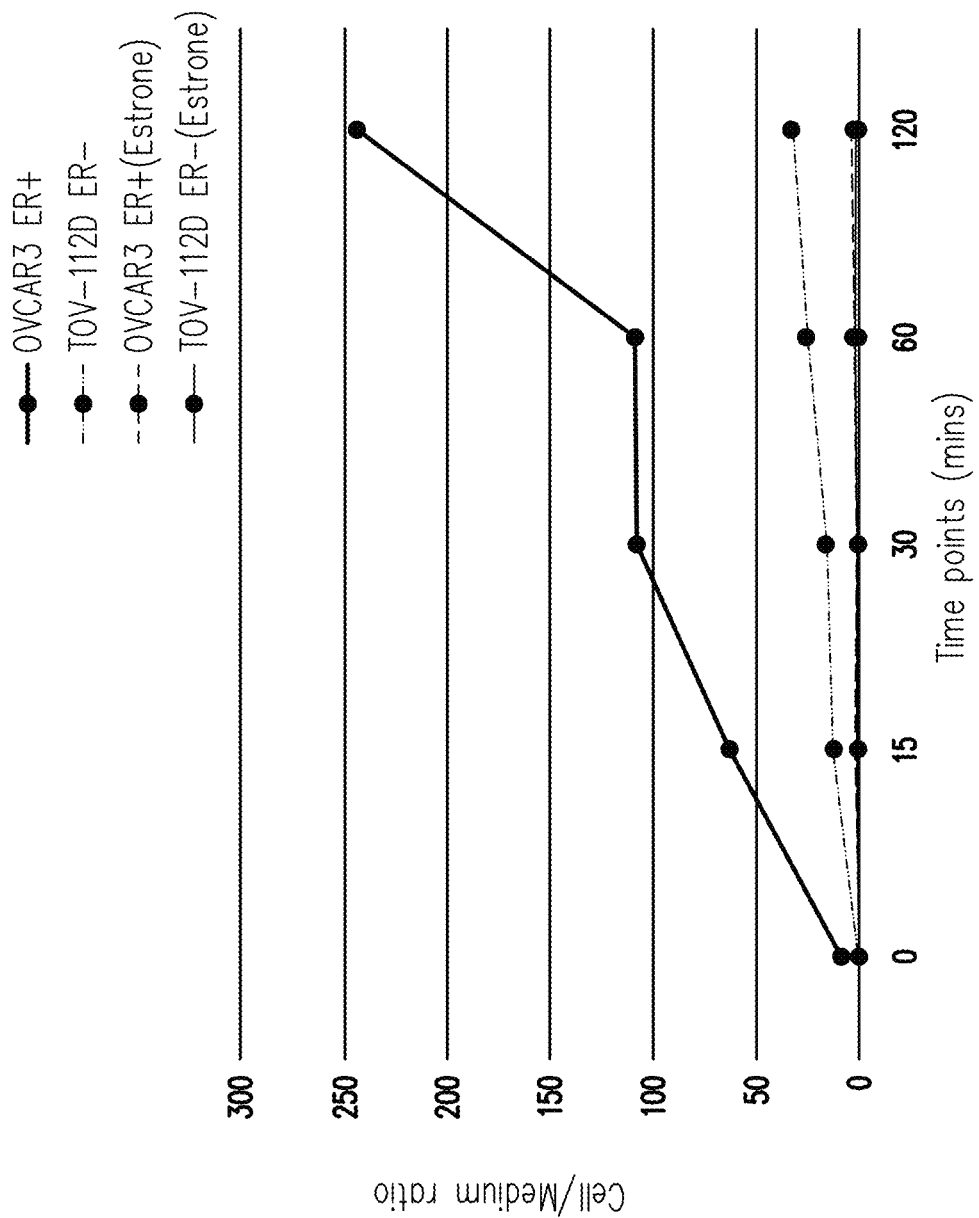
FIG. 5 shows the OVCAR3 cell and TOV-112D cell uptake and blocking studies of Composition $^{99m}$Tc-SC-05-L-1 synthesized in Embodiment 2 of the invention.

FIG. 5 shows the OVCAR3 cell and TOV-112D cell uptake and blocking studies of Composition $^{99m}$Tc-SC-05-L-1 synthesized in Example 4 of the invention. As shown in FIG. 5, the OVCAR3 cell uptake of Composition $^{99m}$Tc-SC-05-L-1 was blocked 80% by estrone indicating an ER mediated process occurred.

Example 6

In Vitro Anti-Cancer Studies
Experiment 3
Effect of Composition SC-05-L-1 and Composition SC-05-K-1 against lymphoma cells was assessed by using cell viability assays in representative mantle cell lines and diffuse large B-cell lymphoma (DLBCL) cell lines.

Figure 6:
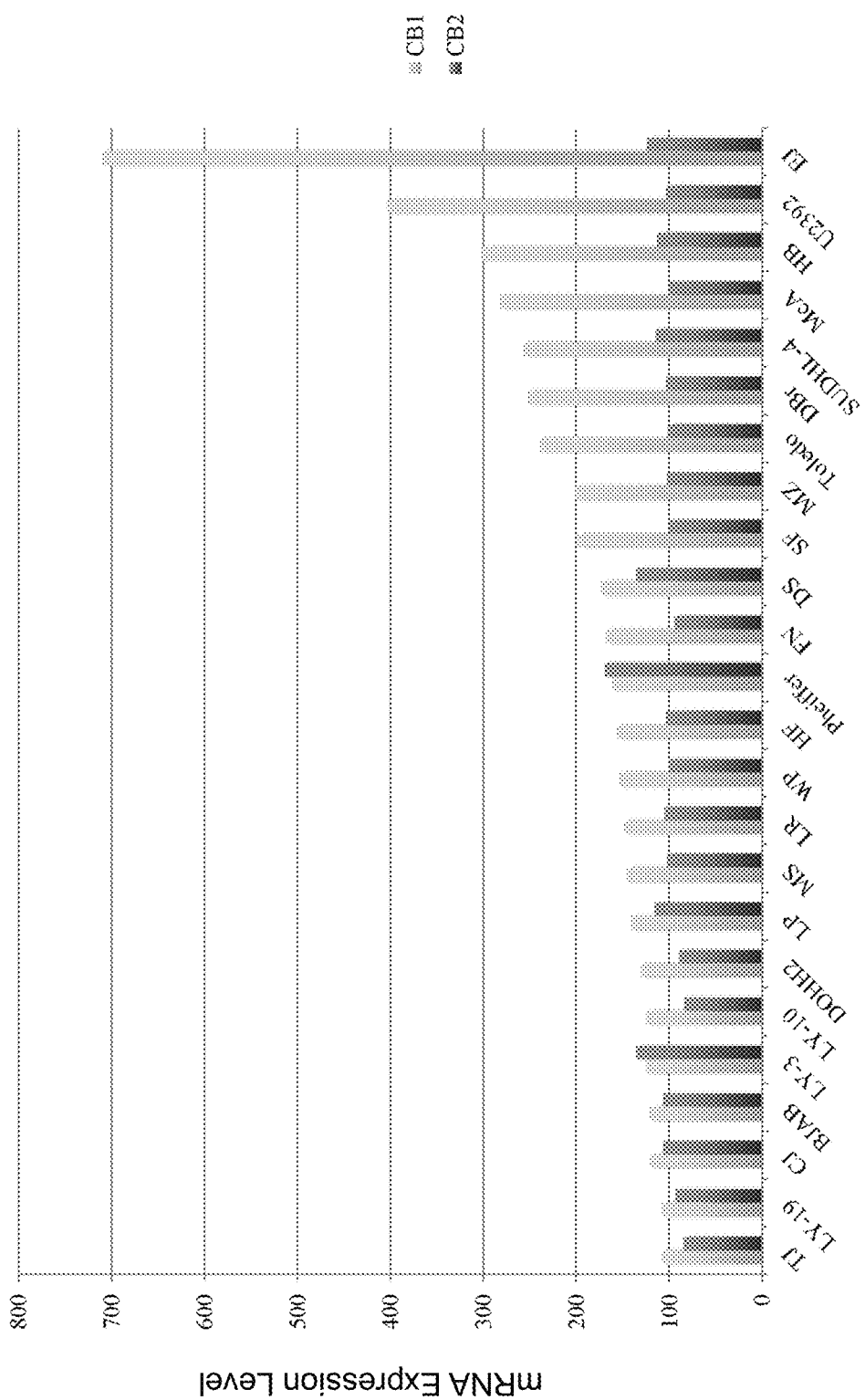
FIG. 6 shows the effect of Composition SC-05-L-1 and Composition SC-05-K-1 against lymphoma cells of the invention.

FIG. 6 shows the effect of Composition SC-05-L-1 and Composition SC-05-K-1 against lymphoma cells of the invention. As shown in FIG. 6, these cell lines were overexpressed with cannabinoid receptors.

Experiment 4
The cells were treated with increasing concentration of Compound SC-05-L-1 and Compound SC-05-K-1. Representative DLBCL cell lines sensitive or less sensitive to Compound SC-05-L-1 and Compound SC-05-K-1 were compared.

Figure 8A:
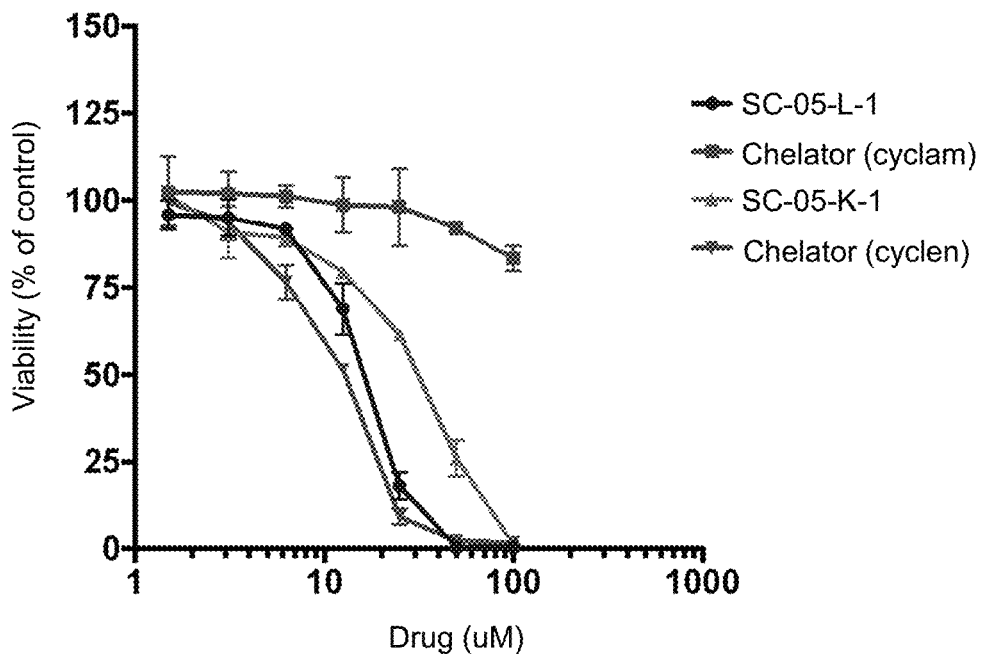
FIG. 8A and FIG. 8B show the in vitro anti-cancer studies of Compound SC-05-K-1 and Compound SC-05-L-1 synthesized in Example 1 and Example 3 of the invention.
Figure 8B:
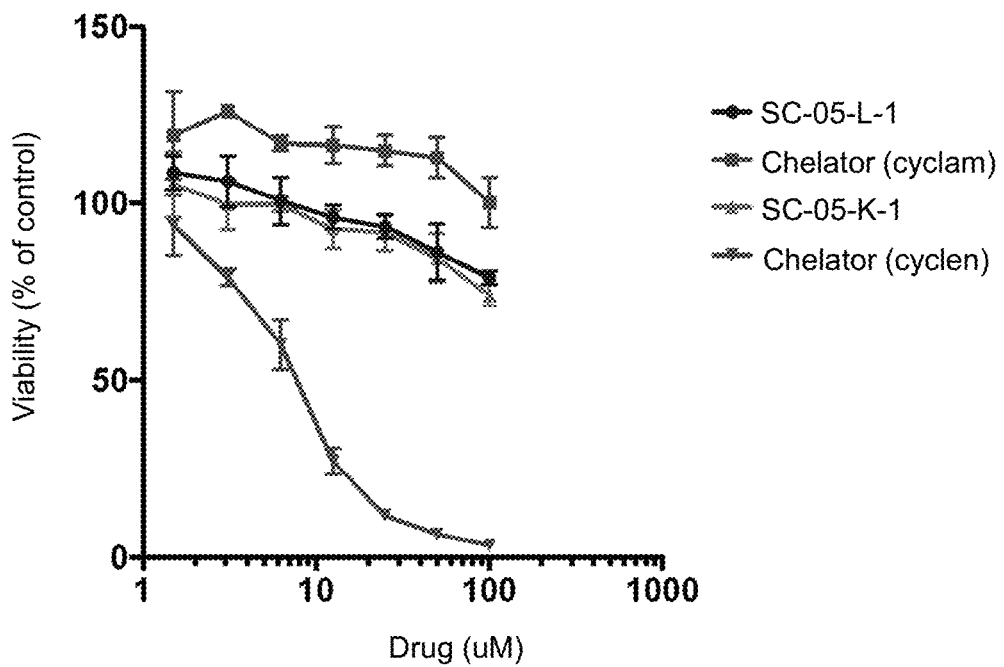

FIG. 7A and FIG. 7B show the in vitro anti-cancer studies of Compound SC-05-L-1 synthesized in Example 3 of the invention. FIG. 8A and FIG. 8B show the in vitro anti-cancer studies of Compound SC-05-K-1 and Compound SC-05-L-1 synthesized in Example 1 and Example 3 of the invention. As shown in FIG. 7A and FIG. 7B, the in vitro anti-cancer studies indicated that Compound SC-05-L-1 had dose-dependent manner against lymphoma cells. As shown in FIG. 8A and FIG. 8B, both Compound SC-05-L-1 and Compound SC-05-K-1 showed similar dose-dependent manner against lymphoma cells. However, Compound SC-05-L-1 is less toxic than Compound SC-05-K-1. In other words, the chelator cyclam is less toxic than chelator cyclen.

In summary, the present invention provides the composition for cross talk between the estrogen receptors and the cannabinoid receptors. The hydroxy group is incorporated in the finished product. In the composition of the present invention, the protected chelator is used as to react the epoxylated receptor ligand to form the chelator-receptor ligand conjugate. The technology platform may exploit conjugating antagonists and agonists and seeing their effects in various forms of diseases. Also, the composition may be further prepared in pharmaceutical formulations and kits using the chemical procedures known to skilled artisans. In addition, the method of synthesizing the composition is also provided, and the synthesis method may obviate the need of adding protecting groups to the receptor ligand and increase process efficiency and purify of the final product. Besides, the composition of the present invention may be used for imaging or treating CBRs and ERs associated diseases.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A composition for cross talk between estrogen receptors and cannabinoid receptors, comprising a conjugate of a chelator and a receptor ligand, and a metal ion,
   wherein the chelator comprises a nitrogen containing tetraazacyclic ring;
   the receptor ligand comprises non-steroidal tamoxifen, wherein in the conjugate, the non-steroidal tamoxifen is joined with the chelator by a —CH$_2$—CH$_2$—CH$_2$—O—CH$_2$—CHOH— group, and in the —CH$_2$—CH$_2$—CH$_2$—O—CH$_2$—CHOH— group, the left terminal —CH$_2$ is directly joined to an ethylene of a triphenylethylene group in the non-steroidal tamoxifen, and the right terminal —CHOH— is joined to the chelator side; and
   wherein the metal ion is $^{99}$mTc, $^{67,68}$Ga, $^{60,61,62,64,67}$Cu, $^{111}$In, $^{166}$Ho, $^{186,188}$Re, $^{90}$Y, $^{177}$Lu, $^{223}$Ra, $^{225}$Ac, and $^{89}$Zr, $^{117}$mSn, $^{153}$Sm, $^{89}$Sr, $^{59}$Fe, $^{212}$Bi, $^{211}$At, $^{45}$Ti, Tc, Sn, Cu, In, Tl, Ga, As, Re, Ho, Y, Sm, Se, Sr, Bi, Fe, Mn, Lu, Co, Pt, Ca, Rh, Eu, Tb, or a combination thereof.

2. The composition according to claim 1, wherein the nitrogen containing tetraazacyclic ring is a cyclam, a cyclen, a cyclam-carboxylic acid, or a cyclen-carboxylic acid.

3. The composition according to claim 1, wherein the composition is a 99mTc-cyclam-tamoxifen analogue or a 99mTc-cyclen-tamoxifen analogue.

4. A kit comprising the composition according to claim 1.

5. A method of synthesizing the composition according to claim 1, which comprises conjugating the receptor ligand to the chelator with an epoxide.

6. The method of synthesizing the composition according to claim 5, wherein the chelator is the nitrogen containing tetraazacyclic ring, and the receptor ligand is conjugated to the tetraazacyclic ring with the epoxide.

7. The method of synthesizing the composition according to claim 5, wherein the epoxide is attached to an aliphatic chain of the receptor ligand.

8. A treatment method for cancer, rheumatoid arthritis, osteoporosis, atherosclerosis, or endometrial tissue comprising administration of the composition according to claim 1.

* * * * *